United States Patent
Klier et al.

(10) Patent No.: US 11,951,115 B2
(45) Date of Patent: Apr. 9, 2024

(54) METHODS OF TREATING RETINAL VASCULOPATHIES

(71) Applicant: Unity Biotechnology, Inc., South San Francisco, CA (US)

(72) Inventors: Sharon Klier, South San Francisco, CA (US); Jamie Dananberg, South San Francisco, CA (US)

(73) Assignee: Unity Biotechnology, Inc., South San Francisco, CA (US)

(*) Notice: Subject to any disclaimer, the term of this patent is extended or adjusted under 35 U.S.C. 154(b) by 0 days.

(21) Appl. No.: 17/719,066

(22) Filed: Apr. 12, 2022

(65) Prior Publication Data

US 2022/0331345 A1 Oct. 20, 2022

Related U.S. Application Data

(60) Provisional application No. 63/325,056, filed on Mar. 29, 2022, provisional application No. 63/309,260, filed on Feb. 11, 2022, provisional application No. 63/237,454, filed on Aug. 26, 2021, provisional application No. 63/174,188, filed on Apr. 13, 2021.

(51) Int. Cl.
  *A61K 31/675* (2006.01)
  *A61K 9/00* (2006.01)
  *A61P 27/02* (2006.01)

(52) U.S. Cl.
  CPC .......... *A61K 31/675* (2013.01); *A61K 9/0019* (2013.01); *A61K 9/0048* (2013.01); *A61P 27/02* (2018.01)

(58) Field of Classification Search
  CPC .......................... A61K 31/635; A61K 31/675
  See application file for complete search history.

(56) References Cited

U.S. PATENT DOCUMENTS

| 10,717,722 B2 * | 7/2020 | Beausoleil .............. A61P 35/00 |
| 10,981,892 B2 * | 4/2021 | Beausoleil .......... C07D 401/14 |
| 11,129,838 B2 * | 9/2021 | Tsuruda ................. A61P 27/02 |
| 2020/0317640 A1 | 10/2020 | Beausoleil et al. |

FOREIGN PATENT DOCUMENTS

| WO | WO 2015/012831 | 1/2015 |
| WO | WO 2020/021447 | 1/2020 |
| WO | WO 2022/099431 | 5/2022 |

OTHER PUBLICATIONS

Opthalmology (1991) "Early Treatment Diabetic Retinopathy Study Design and Baseline Patient Characteristics: ETDRS Report No. 7" Supplement 98(5): 741-756.

PUbchem CID 155164041 (2020) 5-(4-Chlorophenyl)-2-methyl-4-[3-[4-[4-[[4-[[1-phenylsulfanyl-4-( 4-phosphonooxypiperidi n-1-yl)butan-2-yl]amino]-3-(trifluoromethylsulfonyl) phenyl] sulfonylamino] phenyl] pi perazin-1-yl] phenyl]-1-propan-2-ylpyrrole-3-carboxylic acid: 1-10.

* cited by examiner

*Primary Examiner* — Rei Tsang Shiao
(74) *Attorney, Agent, or Firm* — Rudy J. Ng; Bozicevic, Field & Francis LLP

(57) ABSTRACT

The present invention relates to methods of treating certain retinal vasculopathies such as diabetic macular edema, diabetic retinopathy and age-related macular degeneration, among others. The method includes treating a patient suffering from a retinal vasculopathy by administering to the patient a therapeutically effective dose of a compound as disclosed herein.

33 Claims, 15 Drawing Sheets

METHODS OF TREATING RETINAL VASCULOPATHIES

CROSS-REFERENCE TO RELATED APPLICATIONS

This application claim the benefit of U.S. Provisional Application No. 63/174,188, filed Apr. 13, 2021, U.S. Provisional Application No. 63/237,454, filed Aug. 26, 2021, U.S. Provisional Application No. 63/309,260, filed Feb. 11, 2022, and U.S. Provisional Application No. 63/325,056, filed Mar. 29, 2022, the disclosures of which are incorporated herein by reference.

FIELD OF THE INVENTION

The invention relates to methods of treating certain retinal vasculopathies such as diabetic macular edema, diabetic retinopathy and age-related macular degeneration.

BACKGROUND OF THE INVENTION

Pathological angiogenesis remains one of the main challenges in the treatment of certain retinal vasculopathies such as diabetic macular edema (DME), diabetic retinopathy (DR) and age-related macular degeneration (AMD), which are severe diseases often leading to visual loss and blindness.

DME is a complication of diabetic retinopathy (DR) following chronic, poorly controlled diabetes, and is the most common form of sight-threatening retinopathy in people with diabetes (Tan et al. 2016, IDF 2019). Approximately one in 14 patients with diabetes has some degree of DME (Coney 2019). The overall prevalence of DR in patients with diabetes using retinal images was estimated to be 35%, with vision-threatening DR present in 12% (WHO 2015). Prevalence depends on the type of diabetes and the duration of the disease. For both types of diabetes, type 1 diabetes (T1 D) and type 2 diabetes (T2D), after 25 years duration, prevalence approximates 30% (Browning et al. 2018).

Age-related macular degeneration (AMD) is the leading cause of severe vision loss in individuals >55 years of age in the developed world, accounting for 6-9% of legal blindness globally (Wong et al. Lancet Glob. Health (2014); Jonas et al. Asia Pac J. Ophthalmol (2017)). It has been estimated that by 2040, ~288 million people will be affected by AMD worldwide (Wong et al (2014)).

AMD is a multifactorial blinding disease. It has been previously demonstrated that oxidative stress, aging, DNA damage and ultraviolet radiation can lead to AMD by influencing the autophagy function of retinal pigment epithelial (RPE) cells, cellular senescence, and the immune-inflammatory response (Wang et al. Oxid Med Cell Longev. 2019).

Previous standards of care to stabilize vision in patients with such ocular diseases encompassed laser photocoagulation therapy, surgical vitrectomy and photodynamic therapy with verteporfin. Currently, anti-vascular endothelial growth factor (anti-VEGF) therapies and their ability to restore vision in patients suffering from such ocular vascular diseases has been widely used since the approval of Lucentis® (ranibizumab) in 2006 and Eylea® (aflibercept) in 2011.

However, such anti-VEGF treatments often led to off-target effects on healthy blood vessels. Therefore, discerning the molecular discrepancies between healthy and diseased blood vessels would allow for targeted treatments that selectively eliminate pathological vasculature while sparing vessels essential for physiological tissue function.

Another drawback to anti-VEGF standards of care is that they require frequent (e.g., monthly and even bimonthly intravitreal injections) and long-term administration to maintain vision gains (Heier et al. Ophthalmology 2012; 119:2537-48; the Comparison of Age-Related Macular Degeneration Treatment Trials [CATT] Research Group 2016 Ophthalmology 2016; 123:1751-61). This has led to poor patient compliance with this frequent treatment regimen.

There are also evidence of some patients experiencing suboptimal responses to anti-VEGF treatment as well as some patients that do not respond to anti-VEGF treatments at all. See Brown D M, et al., Ophthalmology. 2013; 120:2013-2022; and Nguyen-Khoa B A, et al., BMC Ophthalmol. 2012; 12:11.

Therefore, a need exists for the development of a treatment for retinal vasculopathies having advantages over the standard of care.

SUMMARY OF THE INVENTION

The present invention provides novel methods of treating DME or DR or AMD having advantages over the standard of care.

Specifically contemplated as part of the disclosed invention is:

Embodiment 1. A method of treating a patient suffering from a retinal vasculopathy comprising administering to the patient a therapeutically effective dose of a crystalline solid meglumine salt of a compound of Formula I (Compound-meglumine):

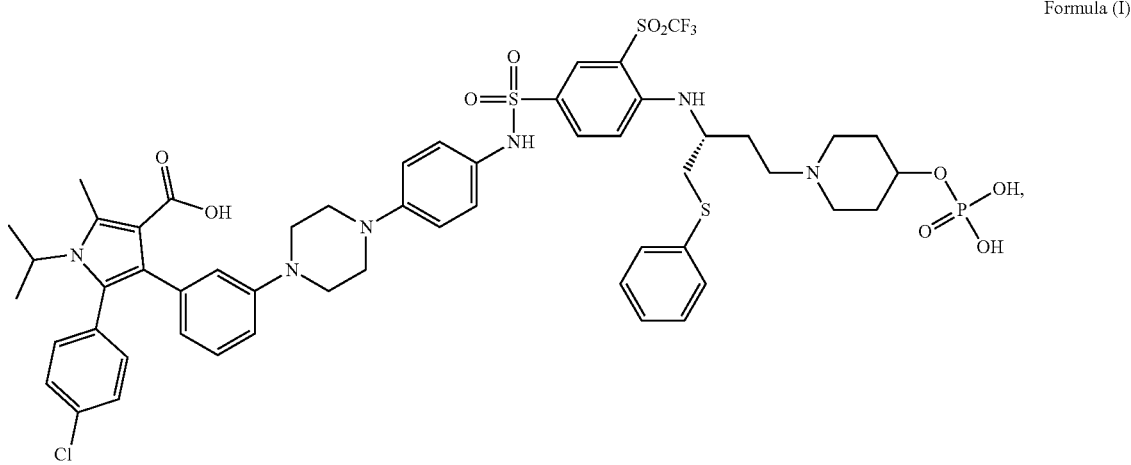

Formula (I)

(R)-5-(4-chlorophenyl)-1-isopropyl-2-methyl-4-(3-(4-(4-((4-((1-(phenylthio)-4-(4-((phosphonooxy)methyl)piperidin-1-yl)butan-2-yl)amino)-3-((trifluoromethyl)sulfonyl)phenyl)sulfonamido)phenyl)piperazin-1-yl)phenyl)-1H-pyrrole-3-carboxylic acid, wherein the therapeutically effective dose is up to 25 ug of the Compound-meglumine per eye.

Embodiment 2. The method of embodiment 1, wherein the meglumine in the crystalline solid meglumine salt of the compound of Formula I is present in a stoichiometric ration of from 1 to 3.

Embodiment 3. The method of embodiment 2, wherein the crystalline solid meglumine salt of the compound of Formula I is stable at a temperature of from 2° C. to 8° C. for 12 months or more.

Embodiment 4. The method of any of embodiments 1-3, wherein the patient has a baseline best corrected visual acuity (BCVA) between 70 to 20 Early Treatment Diabetic Retinopathy Study (ETDRS) letters or a baseline 20/40 to 20/400 on the Snellen chart.

Embodiment 5. The method of any one of embodiments 1-4, wherein the patient had been previously treated with an anti-vascular endothelial growth factor (anti-VEGF) treatment at baseline.

Embodiment 6. The method of embodiment 5, wherein the previous treatment with an anti-VEGF treatment occurred in the preceding 6-month period.

Embodiment 7. The method of embodiment 6, the wherein the patient also presented with a central subfield thickness (CST) of 350 um as measured by SD-OCT at baseline, of 50 μm as measured by SD-OCT at baseline, of 200 μm as measured by SD-OCT at baseline, of 250 μm as measured by SD-OCT at baseline, of 300 as measured by SD-OCT at baseline, of 350 μm as measured by SD-OCT at baseline.

Embodiment 8. The method of any one of embodiments 1-7, wherein the patient has a hemoglobin A1C (HbA1C) of <12% at baseline, of <11% at baseline, of <10% at baseline, of <9% at baseline, of <8% at baseline, of <7% at baseline, of <6% at baseline, of <5% at baseline, of <4% at baseline, of <3% at baseline, of <2% at baseline, of <1% at baseline.

Embodiment 9. The method of any of embodiments 1-8, wherein the patient has an intraocular pressure (IOP) of ≤23 mmHg at baseline, of ≤22 mmHg at baseline, of ≤21 mmHg at baseline, of ≤20 mmHg at baseline, of ≤19 mmHg at baseline, of ≤18 mmHg at baseline, of ≤17 mmHg at baseline, of ≤16 mmHg at baseline, of ≤15 mmHg at baseline, of ≤14 mmHg at baseline, of ≤13 mmHg at baseline, of ≤12 mmHg at baseline, of ≤11 mmHg at baseline, of ≤10 mmHg at baseline, of ≤9 mmHg at baseline, of ≤8 mmHg at baseline, of ≤7 mmHg at baseline, of ≤6 mmHg at baseline, of ≤5 mmHg at baseline, of ≤4 mmHg at baseline, of ≤3 mmHg at baseline, of ≤2 mmHg at baseline, of ≤1 mmHg at baseline.

Embodiment 10. The method of any one of embodiments 1-19, wherein the therapeutically effective dose of the Compound-meglumine is 0.5 ug, 1 ug, 2 ug, 2.5 ug, 3 ug, 4 ug, 5 ug, 6 ug, 7 ug, 8 ug, 9 ug, 10 ug, 11 ug, 12 ug, 13 ug, 14 ug, 15 ug, 16 ug, 17 ug, 18 ug, 19 ug, 20 ug, 21 ug, 22 ug, 23 ug, 24 ug or 25 ug per eye.

Embodiment 11. The method of any one of embodiments 1-10, wherein the therapeutically effective dose of the Compound-meglumine is between 0.5 μg-1 μg per eye, between 1-2 μg per eye, between 2-2.5 μg per eye, between 2.5 μg-3 per eye, between 3-4 μg per eye, between 4-5 μg per eye, between 5-6 per eye, between 6-7 μg per eye, between 7-8 μg per eye, between 8-9 μg per eye, between 9-10 μg per eye, between 10-11 μg per eye, between 11 μg-12 μg per eye, between 12-13 μg per eye, between 13-14 μg per eye, between 14-15 μg per eye, between 15-16 μg per eye, between 16-17 per eye, between 17-18 μg per eye, between 18-19 μg per eye, between 19-20 μg per eye, between 20 μg-21 μg per eye, between 21 μg-22 μg per eye, between 22 μg-23 μg per eye, between 23 μg-24 μg per eye or between 24 μg-25 per eye.

Embodiment 12. The method of any one of embodiments 1-11, wherein the therapeutically effective dose of the Compound-meglumine is between 0.5-2 ug per eye, is between 2-4 ug per eye, is between 3-5 ug per eye, is between 4-6 ug per eye, is between 5-7 ug per eye, is between 6-8 ug per eye, is between 7-9 ug per eye, is between 8-10 ug per eye, is between 9-11 ug per eye, is between 10-15 ug per eye, is between 15-20 ug per eye, is between 20-25 ug per eye.

Embodiment 13. The method of any one of embodiments 1-12, wherein the Compound-meglumine is administered into the patient's eye first as a loading dose, prior to administering the therapeutically effective dose.

Embodiment 14. The method of embodiment 13, wherein the loading dose of the Compound-meglumine is between 0.5 μg-1 μg per eye, between 1-2 μg per eye, between 2-2.5 μg per eye, between 2.5 μg-3 μg per eye, between 3-4 μg per eye, between 4-5 μg per eye, between 5-6 μg per eye, between 6-7 per eye, between 7-8 μg per eye, between 8-9 μg per eye, between 9-10 per eye, between 10-11 μg per eye, between 11 μg-12 μg per eye, between 12-13 μg per eye, between 13-14 μg per eye, between 14-15 μg per eye, between 15-16 μg per eye, between 16-17 μg per eye, between 17-18 per eye, between 18-19 μg per eye, between 19-20 μg per eye, between 20-21 μg per eye, between 21 μg-22 μg per eye, between 22 μg-23 μg per eye, between 23 μg-24 μg per eye or between 24 μg-25 μg per eye.

Embodiment 15. The method of embodiment 13, wherein the loading dose of the Compound-meglumine is between 0.5-2 ug per eye, is between 2-4 ug per eye, is between 3-5 ug per eye, is between 4-6 ug per eye, is between 5-7 ug per eye, is between 6-8 ug per eye, is between 7-9 ug per eye, is between 8-10 ug per eye, is between 9-11 ug per eye, is between 10-15 ug per eye, is between 15-20 ug per eye, is between 20-25 ug per eye.

Embodiment 16. The method of any one of embodiments 13-15, wherein the loading dose of the Compound-meglumine is in a total volume of 50 ul per eye.

Embodiment 17. The method of any one of embodiments 1-13, wherein the therapeutically effective dose of the Compound-meglumine is administered intravitreally into the patient's eye.

Embodiment 18. The method of any one of embodiments 14-16, wherein the loading dose of the Compound-meglumine is administered intravitreally into the patient's eye.

Embodiment 19. The method of any of embodiments 1-12, 17, wherein the therapeutically effective dose of the Compound-meglumine is administered intravitreally into the patient's eye every 2 months, every 3 months, every 4 months, every 5 months, every 6 months, every 7 months, every 8 months, every 9 months, every 10 months, every 11 months, every 12 months.

Embodiment 20. The method of any of embodiments 1-12, 17, wherein the therapeutically effective dose of the Compound-meglumine is administered intravitreally into the patient's eye between every 2-3 months, between every 3-4 months, between every 5-6 months, between every 6-7 months, between every 8-9 months, between every 9-10 months, between every 11-12 months.

Embodiment 21. The method of any of embodiments 1-12, 17, 19-20, wherein the therapeutically effective dose of the Compound-meglumine is administered intravitreally into the patient's eye as a single dose every 2 months, a single dose every 3 months, a single dose every 4 months, a single dose every 5 months, a single dose every 6 months, a single dose every 7 months, a single dose every 8 months, a single dose every 9 months, a single dose every 10 months, a single dose every 11 months, or a single dose every 12 months.

Embodiment 22. The method of any of embodiments 1-12, 17, 19-20, wherein the therapeutically effective dose of the Compound-meglumine is administered intravitreally into the patient's eye as a single dose between every 2-3 months, as a single dose between every 3-4 months, as a single dose between every 5-6 months, as a single dose between every 6-7 months, as a single dose between every 8-9 months, as a single dose between every 9-10 months, as a single dose between every 11-12 months.

Embodiment 23. The method of any of embodiments 1-12, 17, 20-22, wherein the therapeutically effective dose of the Compound-meglumine is administered intravitreally into the patient's eye once as a single dose.

Embodiment 24. The method of embodiment 23, wherein the therapeutically effective dose of the Compound-meglumine is administered intravitreally into the patient's eye once as a single dose is not in conjunction with a prior loading dose.

Embodiment 25. The method of any of embodiments 13-16, 18, wherein the loading dose, administered intravitreally into the patient's eye, is administered as one monthly IVT injection for 2 months, or one monthly IVT injection for 3 months, or at least one IVT injection over 2 months, or at least two IVT injections over 2 months, or at least three IVT injections over 2 months, or at least three IVT injections over 3 months, or at least two IVT injections over 3 months.

Embodiment 26. The method of embodiment 25, wherein the loading dose is followed by a gap of treatment of at least 2 months, of at least 3 months, of at least 4 months, of at least 5 months, of at least 6 months, of at least 7 months, of at least 8 months, of at least 9 months, of at least 10 months, of at least 11 months, of at least 12 months, before administering the therapeutically effective dose.

Embodiment 27. The method of any of embodiments 1-26, wherein the patient demonstrates a CST reduction of at least 40 µm from baseline, 50 µm from baseline, at least 60 µm from baseline, at least 70 µm from baseline, at least 80 µm from baseline, at least 90 µm from baseline, as measured by SD-OCT.

Embodiment 28. The method of any of embodiments 1-27, wherein the patient further demonstrates an absence of macular fluid as assessed by SD-OCT as compared to baseline.

Embodiment 29. The method of any of embodiments 1-27, wherein the patient further demonstrates an absence of exudation as assessed by SD-OCT as compared to baseline.

Embodiment 30. The method of any of embodiments 1-29, wherein the patient does not require more than 2 anti-VEGF treatment rescue, or does not require more than 3 anti-VEGF treatment rescue, or does not require more than 4 anti-VEGF treatment rescue, or does not require more than 5 anti-VEGF treatment rescue.

Embodiment 31. The method of embodiment 30, wherein the patient does not require any anti-VEGF treatment rescue.

Embodiment 32. The method of any of embodiments 1-31, wherein the patient demonstrates an improvement in at least 5 ETDRS letter improvement on BCVA over baseline, at least 6 ETDRS letter improvement on BCVA over baseline, at least 7 ETDRS letter improvement on BCVA over baseline, at least 8 ETDRS letter improvement on BCVA over baseline, at least 9 ETDRS letter improvement on BCVA over baseline, at least 10 ETDRS letter improvement on BCVA over baseline, at least 15 ETDRS letter improvement on BCVA over baseline, or at least 20 ETDRS letter improvement on BCVA over baseline.

Embodiment 33. The method of any of embodiments 1-32, wherein the patient demonstrates an improvement of between 5-7 ETDRS letter improvement on BCVA over baseline, of between 6-8 ETDRS letter improvement on BCVA over baseline, of between 7-9 ETDRS letter improvement on BCVA over baseline, of between 10-15 ETDRS letter improvement on BCVA over baseline, of between 15-20 ETDRS letter improvement on BCVA over baseline, of between 20-25 ETDRS letter improvement on BCVA over baseline, of between 25-30 ETDRS letter improvement on BCVA over baseline.

Embodiment 34. The method of any of embodiments 1-43, wherein the patient demonstrates at least a 0.10 mm$^2$ reduction of ocular avascular area over baseline, or at least a 0.20 mm$^2$ reduction of ocular avascular area over baseline, or at least a 0.30 mm$^2$ reduction of ocular avascular area over baseline, or at least a 0.40 mm$^2$ reduction of ocular avascular area over baseline, or at least a 0.50 mm$^2$ reduction of ocular avascular area over baseline, or at least a 0.60 mm$^2$ reduction of ocular avascular area over baseline, or at least a 0.70 mm$^2$ reduction of ocular avascular area over baseline, or at least a 0.80 mm$^2$ reduction of ocular avascular area over baseline, or at least a 0.90 mm$^2$ reduction of ocular avascular area over baseline, or at least a 1.0 mm$^2$ reduction of ocular avascular area over baseline, all as measured by fluorescence angiography (FA) or optical coherence tomography angiography (OCT-A).

Embodiment 35. The method of any of embodiments 1-34, wherein the patient has a 2-step improvement in diabetic retinopathy severity scale (DRSS) over baseline.

Embodiment 36. The method of any of embodiments 1-35, wherein the patient demonstrates a regression in neovascularization over baseline, as measured by FA or OCT-A.

Embodiment 37. The method of any of embodiments 1-36, wherein the retinal vasculopathy is diabetic macular edema (DME).

Embodiment 38. The method of any of embodiments 1-36, wherein the retinal vasculopathy is diabetic retinopathy (DR).

Embodiment 39. The method of any of embodiments 1-36, wherein the retinal vasculopathy is age-related macular degeneration (AMD).

Embodiment 40. The method of any of embodiment 39, wherein the retinal vasculopathy is geographic atrophy (GA).

Embodiment 41. The method of embodiment 38, wherein the patient also presented with nonproliferative diabetic retinopathy at baseline.

Embodiment 42. The method of embodiment 38, wherein the patient also presented with proliferative diabetic retinopathy at baseline.

DETAILED DESCRIPTION OF THE INVENTION

I. Definitions

Figure 1:
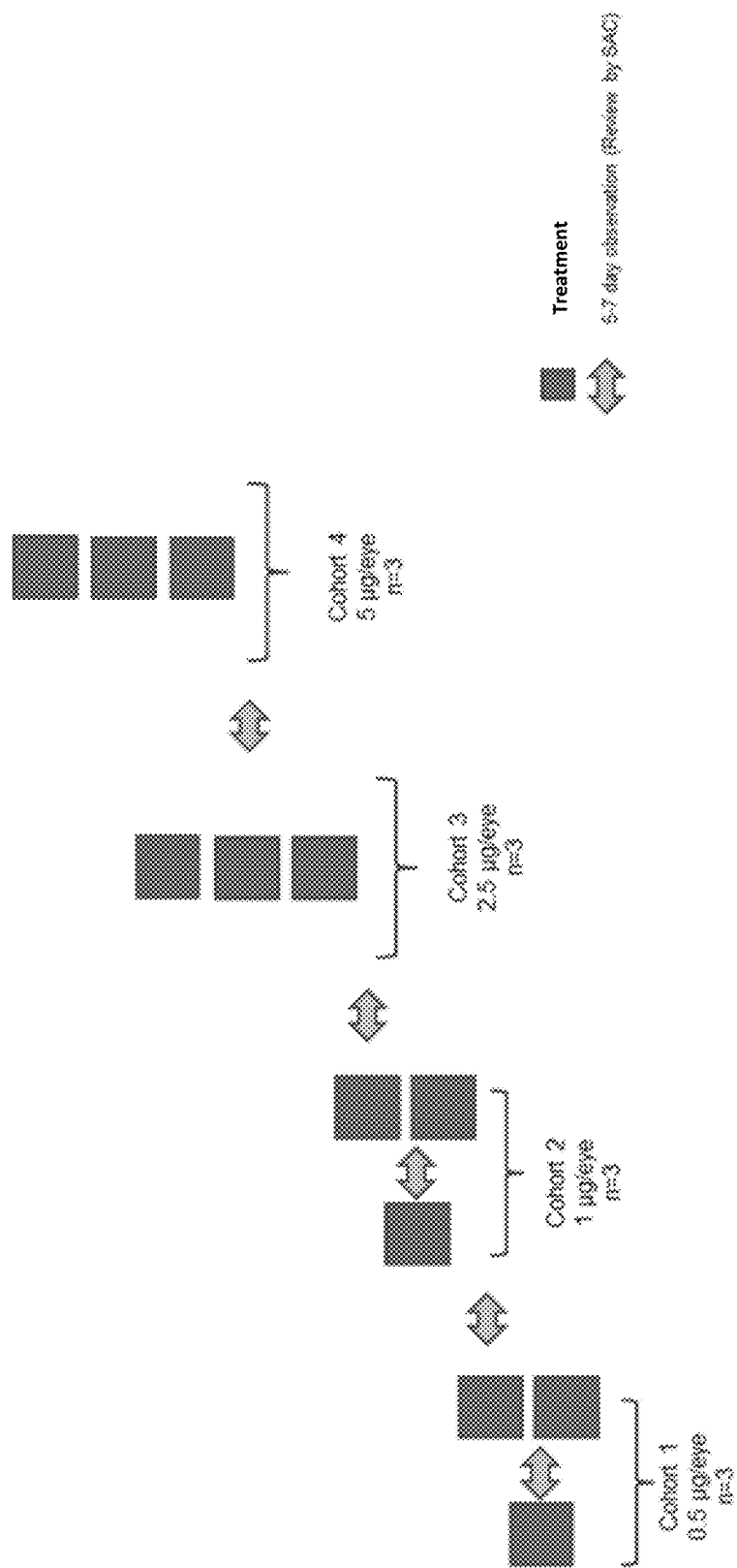
FIG. 1 depicts a schematic of the Phase I single ascending dose escalation, safety and toxicity study as described in Example 1.

The term "about" as used herein refers to the usual error range for the respective value readily known to the skilled person in this technical field. Reference to "about" a value or parameter herein includes (and describes) embodiments that are directed to that value or parameter per se.

As used herein, "administering" is means a method of giving a dosage of the Compound-meglumine to a patient suffering from the retinal vasculopathies herein. The compositions utilized in the methods described herein can be administered, for example, intravitreally (e.g., by intravitreal injection), ocularly (e.g., by ocular injection), or intraocularly (e.g., by intraocular injection). The method of administration can vary depending on various factors (e.g., the compound or composition being administered, and the severity of the condition, disease, or disorder being treated).

As used herein, the term "anti-VEGF treatment" or "anti-VEGF therapy" means any currently approved anti-VEGF drugs indicated to treat retinal vasculopathies. Such approved drugs include, for example, Lucentis® (ranibizumab) or Eylea® (aflibercept) and any approved biosimilar drugs to ranibizumab or aflibercept.

As used herein, the term "baseline" as it relates to the patient indicates the patient diagnosis as presented to the attending health care professional prior to treatment with the present invention.

As used herein, "best-corrected visual acuity" (BCVA) refers to the measurement of the best vision correction that can be achieved using glasses or contact lenses. It can be measured using the Early Treatment Diabetic Retinopathy Study (ETDRS) protocol.

As used herein, "CST" stands for changes in central subfield thickness, also known as foveal thickness, which is defined as the average thickness of the macula in a central 1 mm grid. Average macular thickness is defined as the mean of thicknesses in nine sections. A clinically meaningful change in CST can be a reduction of, for example, between 50 µm to 100 µm, as compared to baseline.

As used herein, "Early Treatment Diabetic Retinopathy Study" (ETDRS), as used in association with letter improvement, is a type of measurement used to assess visual acuity, in which a geometric progression of the symbols or letters used on the chart called a logarithmic minimum angle of resolution (log MAR). Each line contains the same number of symbols or letters, with each line value equaling 0.1 log unit, or 25%, smaller than the preceding line (when starting at the top of the chart). The patient is asked to read a series of letters of known height at a prescribed distance, with the smallest legible letters read indicating the degree of near or far acuity. This standardization allows for consistency in evaluation of near and far acuity levels. Normal vision is considered 80 ETDRS letters at 4 meters distance. Clinically meaningful improvement in ETDRS is an increase in between 10-15 ETDRS letters at 4 meters distance as compared to baseline.

As used herein, "exudate" or "retinal exudate" refers to lipid residues that leak from damaged capillaries that can present in patients with DR, DME or AMD. Specifically, an exudate that presents in an AMD patient can be subretinal fluid (SRF). This comes from leaking abnormal blood vessels under the macula. Alternatively, an exudate that presents in an AMD patient can be intraretinal fluid (IRF) which is an increased retinal thickening associated with a reduction in retinal tissue reflectivity on OCT. Finally, an exudate that presents in an AMD patient can be a cystoid edema. This multiple cyst-like (cystoid) areas of fluid appear in the macula and cause retinal swelling or edema.

As used herein, "spectral domain optical coherence tomography" (SD-OCT) is a technique that provides high resolution structural images with precise retinal thickness measurements. It is the technique of choice for early detection of macular edema or retinal exudate and for follow-up of diabetic maculopathy.

As used herein, "hemoglobin A1c" (HbA1C) is a test that indicates a patient's average level of blood sugar over the past 2 to 3 months. It is also called a glycated hemoglobin test or a glycohemoglobin. HbA1C is commonly used to diagnose prediabetes and diabetes. Generally, a normal HbA1C level is below 5.7%, a level of 5.7% to 6.4% generally indicates prediabetes, and a level of 6.5% or more generally indicates diabetes.

As used herein, "intraocular pressure" (IOP) is the fluid pressure inside the eye. Measured values of IOP are influenced by corneal thickness and rigidity. In general, normal intraocular pressure is understood to be between 10 mmHg and 20 mmHg.

As used herein, "patient" if used alone (e.g., " . . . a patient who is treated with a therapeutically effective dose of the Compound-meglumine . . . ") means a patient suffering from a retinal vasculopathy. In contrast, a "DME patient" means a patient who suffers from the specific retinal vasculopathy, DME. Further, an "AMD patient" means a patient who suffers from the specific retinal vasculopathy, AMD. Further, a "DR patient" means a patient who suffers from the specific retinal vasculopathy, DR.

As used herein, "retinal vasculopathies" refers to ocular diseases that involve pathogenic angiogenesis, such as, for example, diabetic macular edema, diabetic retinopathy and age-related macular degeneration. Other ocular diseases can include, for example, geographic atrophy.

As used herein, "treatment" (and "treat" or "treating") refers to clinical intervention in an attempt to alter the natural course of the individual being treated and can be performed either for prophylaxis or during the course of clinical pathology. Desirable effects of the methods of treatment as claimed herein include, but are not limited to, preventing occurrence or recurrence of DME, DR or AMD, alleviation of symptoms of DME, DR or AMD, diminishment of any direct or indirect pathological consequences of DME, DR or AMD, decreasing the rate of disease progression in DME, DR or AMD, amelioration or palliation of the disease state in DME, DR or AMD, and remission or improved prognosis for DME, DR or AMD.

Compositions and Methods

The invention provides methods for treating certain retinal vasculopathies, such as diabetic macular edema (DME), diabetic retinopathy (DR), and age-related macular degeneration (AMD).

DME is a complication of diabetic retinopathy (DR) following chronic, poorly controlled diabetes, and is the most common form of sight-threatening retinopathy in people with diabetes. Approximately one in 14 patients with diabetes has some degree of DME. The World Health Organization reported in 2015 that the overall prevalence of DR in patients with diabetes using retinal images was estimated to be 35%, with vision-threatening DR present in 12%. Prevalence depends on the type of diabetes and the duration of the disease. For both types of diabetes, type 1 diabetes and type 2 diabetes, after 25 years duration, prevalence approximates 30%. In the US, at least 5.5 million individuals over the age of 40 are estimated to have DR in the absence of DME, and an additional 800,000 to 1 million patients have DME. According to some estimates, only 40% of them diagnosed and treated, and about 5% are diagnosed and observed.

Diabetic macular edema (DME), a macular thickening secondary to diabetic retinopathy (DR), results from a blood-retinal barrier defect that leads to vascular leakage and fluid accumulation. See Bhagat N, et al., Sury Ophthalmol. 2009; 54:1-32. DME has been related to the expression of several inflammatory factors, including vascular endothelial growth factor (VEGF), intercellular adhesion molecule-1 (ICAM-1), interleukin-6 (IL-6), monocyte chemotactic protein-1 (MCP-1), and leukostasis. See Funatsu H, et al., Ophthalmology. 2009; 116:73-79; and Miyamoto K, et al., Proc Natl Acad Sci USA. 1999; 96:10836-10841. Moreover, the expression of these factors has been related to both vascular permeability of the retina along with the severity of disease, thus confirming their important pathogenetic role.

DR: The prevalence of diabetic retinopathy increases with age and is the most common cause of blindness in people over the age of 50. It is a multifactorial disorder, with hyperglycemia exerting toxic effects on cells and inflammatory cytokine implicated in many aspects of diabetic eye disease. Diabetic retinopathy involves thickening of capillary basement membranes and prevents pericytes from contacting endothelial cells of the capillaries. Loss of pericytes increases leakage of the capillaries and can lead to a breakdown of the blood-retina barrier. Weakened capillaries can lead to aneurysm formation and further leakage. The duration and severity of hyperglycemia is a factor linked to the development of diabetic retinopathy. These effects of hyperglycemia can also impair neuronal functions in the retina. This is an early stage of diabetic retinopathy termed nonproliferative diabetic retinopathy.

Diabetic retinopathy is also a degenerative disease of the neural retina, associated with alterations in neuronal function prior to the onset of clinical vascular disease. Retinal capillaries can become occluded in diabetes causing areas of ischemia in the retina. The non-perfused tissue responds by eliciting new blood vessel growth from existing vessels (i.e., angiogenesis). These new blood vessels can also cause loss of sight, a condition called proliferative diabetic retinopathy, since the new blood vessels are fragile and tend to leak blood into the eye. In advanced proliferative diabetic retinopathy, an angiogenic, VEGF-mediated response with retinal neovascularization ensues, placing the eye at further risk for severe visual loss due to the development of vitreous hemorrhage or traction retinal detachment. Irreversible vascular or neuronal damage is possible without treatment, underscoring the need for early intervention.

AMD: Age-related macular degeneration (AMD) is a leading cause of visual impairment and severe vision loss. It ranks third among the global causes of visual impairment with a blindness prevalence of 8.7%.

AMD is caused by the deterioration of the central portion of the retina and is a multifactorial disorder, with dysregulation in the complement, lipid, angiogenic, inflammatory, and extracellular matrix pathways implicated in its pathogenesis. AMD pathology is characterized by a progressive accumulation of characteristic yellow deposits, called drusen (e.g., a buildup of extracellular proteins and lipids), in the macula, between the retinal pigment epithelium and the underlying choroid which is believed to damage the retina over time.

There are two basic types of AMD: "dry" and "wet." Approximately 85% to 90% of the cases of AMD are the "dry" (atrophic) type, or geographic atrophy (GA), while 10-15% are the "wet" (exudative) type or neovascular AMD (nAMD). Dry AMD is defined by the gradual loss of retinal pigment epithelial (RPE) and photoreceptor cells in the macula. Patients who are affected by dry AMD have gradual loss of central vision due to the death of photoreceptor cells and their close associates, retinal pigmented epithelial (RPE) cells, with deposition of drusen. Wet AMD is characterized by the growth of abnormal blood vessels beneath the macular epithelium. Wet AMD results in vision loss due to abnormal blood vessel growth (e.g., choroidal neovascularization) in the choriocapillaris, through Bruch's membrane. Clinically, it is classified as early-stage (medium-sized drusen and retinal pigmentary changes) to late-stage (neovascular and atrophic).

Compositions of the invention: It was recently shown that pathological vasculature in the retina selectively engages cellular senescence (see Crespo-Garcia et al., Cell Metabolism 2021, 33,1-15). A senolytic Bcl-xL inhibitor has been developed with the potential to remove senescent cells from a tissue without altering the healthy resident cells in the eye, for administration to patients suffering from DME, DR and AMD. In this way, proinflammatory factors, namely senescence-associated secretory phenotype (SASP) which are secreted by such senescent cells, are selectively removed.

In some embodiments of the claimed invention the compound used to treat a patient suffering from DME or DR or AMD is a crystalline solid meglumine salt of the compound of Formula I (a.k.a., "Compound-meglumine"), where Formula I is:

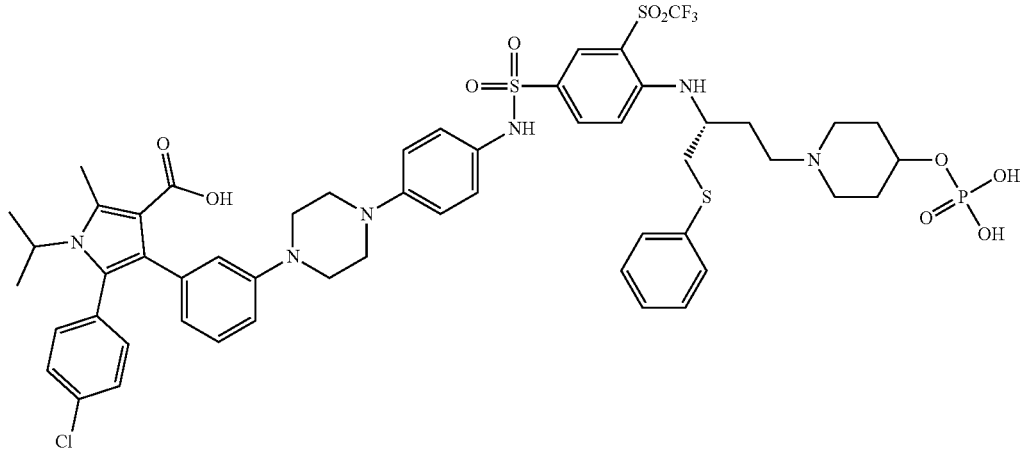

The compound of Formula I is also referred to as (R)-5-(4-chlorophenyl)-1-isopropyl-2-methyl-4-(3-(4-(4-((4-((1-(phenylthio)-4-(4-((phosphonooxy)methyl)piperidin-1-yl) butan-2-yl)amino)-3-((trifluoromethyl)sulfonyl)phenyl) sulfonamido)phenyl)piperazin-1-yl)phenyl)-1H-pyrrole-3-carboxylic acid. In other embodiments of the claimed invention Compound-meglumine is used to treat a patient suffering from DME, DR, or AMD, where the meglumine is present in a stoichiometric ratio of from 1 to 3. In another embodiment, Compound-meglumine is stable at a temperature of from 2° C. to 8° C. for 12 months or more. See International Application PCT/CN2020/127666, which is incorporated by reference in its entirety.

Figure 15:
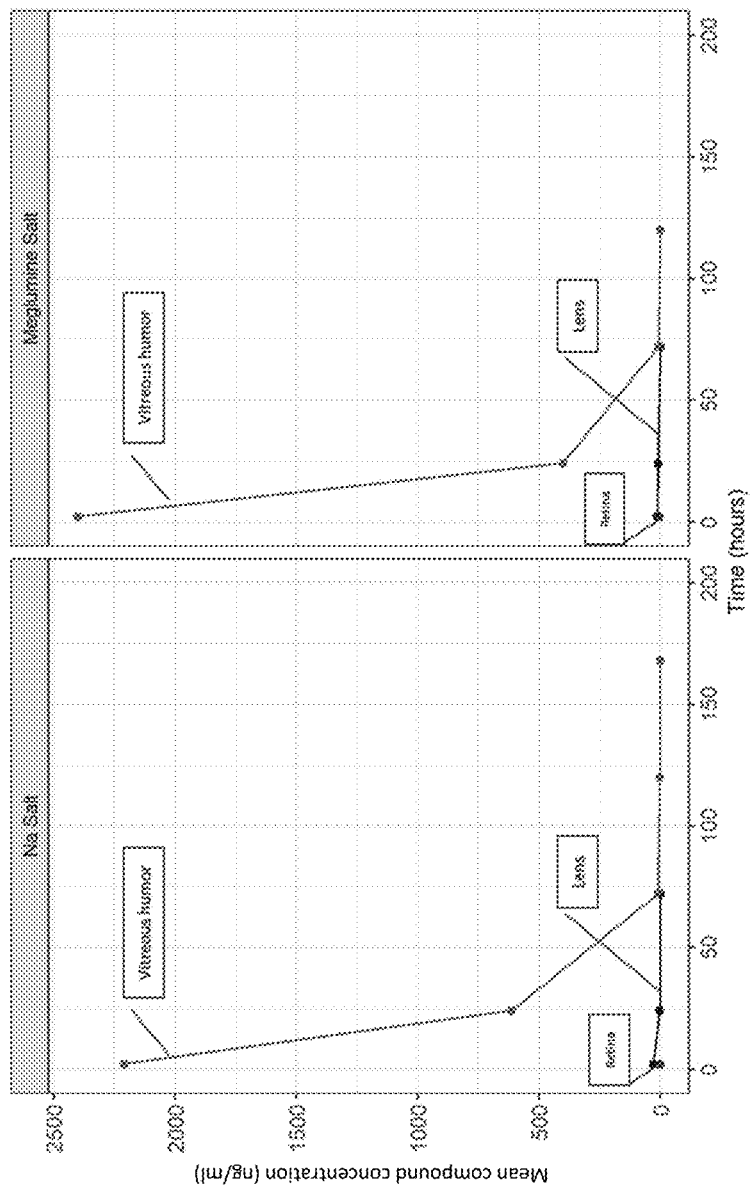
FIG. 15 shows the comparison of the distribution of both the sodium salt form (Na salt) as compared to the meglumine salt form in the vitreous humor, the retina and the lens of New Zealand white rabbits. See Example 4 and Table 1.

The Compound of Formula I is a sodium salt form. It was shown to be unstable at 2-8° C. As a potential commercial therapeutic, such instability is not viable. Therefore, a more stable salt form of the compound was generated, the Compound-meglumine, as disclosed in PCT/CN2020/127666. The pharmacokinetics of the Compound-meglumine was compared to that of the sodium salt form of the Compound of Formula I in order to enable bridging data to regulatory authorities to allow for a substitution of the Compound of Formula I with the Compound-meglumine in clinical trials and beyond without compromise to patient safety or efficacy. See Example 4, FIG. 15 and Table 1.

Dose: In some embodiments of the claimed invention, the therapeutically effective dose of the Compound-meglumine, as described above, used to treat a DME, a DR, an AMD patient is about 0.5 μg per eye, about 1 μg per eye, about 2 μg per eye, about 2.5 μg per eye, about 3 μg per eye, about 4 μg per eye, about 5 μg per eye, about 6 μg per eye, about 7 μg per eye, about 8 μg per eye, about 9 μg per eye, about 10 μg per eye, about 11 μg per eye, about 12 μg per eye, about 13 μg per eye, about 14 μg per eye, about 15 μg per eye, about 16 μg per eye, about 17 μg per eye, about 18 μg per eye, about 19 μg per eye, about 20 μg per eye, about 21 μg per eye, about 22 μg per eye, about 23 μg per eye, about 24 μg per eye or about 25 μg per eye. In other embodiments, the therapeutically effective dose of the Compound-meglumine as described above, is in a total volume of 50 μl per eye.

In some embodiments of the claimed invention, the therapeutically effective dose of the Compound-meglumine, as described above, used to treat DME, DR, or AMD is between 0.5 μg-1 μg per eye, between 1-2 μg per eye, between 2-2.5 μg per eye, between 2.5 μg-3 μg per eye, between 3-4 μg per eye, between 4-5 per eye, between 5-6 μg per eye, between 6-7 μg per eye, between 7-8 μg per eye, between 8-9 μg per eye, between 9-10 μg per eye, between 10-11 per eye, between 11 μg-12 μg per eye, between 12-13 μg per eye, between 13-14 μg per eye, between 14 μg-15 μg per eye, between 15 μg-16 μg per eye, between 16 μg-17 μg per eye, between 17-18 μg per eye, between 18-19 per eye, between 19-20 μg per eye, between 20 μg-21 μg per eye, between 21-22 μg per eye, between 22 μg-23 μg per eye, between 23 μg-24 μg per eye or between 24 μg-25 μg per eye. In other embodiments, the therapeutically effective dose of the Compound-meglumine as described herein, is in a total volume of 50 μl per eye.

In other embodiments of the claimed invention, the therapeutically effective dose of the Compound-meglumine, described above, used to treat DME, DR, or AMD is between 0.5-2 μg per eye, is between 2-4 μg per eye, is between 3-5 μg per eye, is between 4-6 μg per eye, is between 5-7 μg per eye, is between 6-8 μg per eye, is between 7-9 μg per eye, is between 8-10 μg per eye, is between 10-15 μg per eye, is between 15-20 μg per eye, is between 20-25 μg per eye. In other embodiments, the therapeutically effective dose of the Compound-meglumine as described herein, is in a total volume of 50 μl per eye.

Methods of monitoring and diagnosing retinal vasculopathies: Standardized ophthalmic examination techniques known in the art include, for example, a detailed slit lamp biomicroscopic evaluation which allows evaluation of the lids, ocular adnexa, lashes, corneal surface, anterior chamber, pupils, lens, vitreous cavity and central retinal anatomy including the optic nerve and macula. Another method is gonioscopy which allows detailed examination of the anterior chamber angle. Indirect ophthalmoscopy allows for evaluation of the retinal periphery, important in the monitoring of vitreous and peripheral retinal disorders.

Functional tests of visual acuity are known in the art and include, for example, best corrected acuity, contrast acuity, and low luminance acuity, color vision (including Ishihara and Farnsworth Munsell tests) and visual field evaluation (including Humphrey automated perimetry and microperimetry), tear production (Schirmer test), and tonometry to measure intraocular pressure (IOP). These are used in conjunction with structural tests, which include, for example, anterior and posterior segment photographs, corneal pachymetry, ultrasound, ultrasound biomicroscopy, optical coherence tomography (OCT), optical coherence tomography angiography (OCTA), fluorescence angiography (FA), intravenous fluorescein angiography (IVFA), and fundus autofluorescence (FAF). Imaging such as computerized tomography (CT) or magnetic resonance imaging (MRI) scans are utilized to evaluate ocular, periocular and orbital structures, and the intracranial portion of the optic nerve, visual pathway and visual cortex in the brain. These tests allow visualization of structural integrity and thickness of the layers of the eye and surrounding structures, and assessment of blood flow and circulation. Advanced functional testing of the retina, optic nerve and visual pathway/cortex is also used, including electrophysiologic tests such as full field and multifocal electroretinography, visual evoked potentials and microperimetry to diagnose and monitor disease progression and impact of therapy. Those of skill in the art will be able to deploy the appropriate methodologies known in the art to diagnose, measure and monitor the retinal vasculopathies described herein.

Patient: In some embodiments of the claimed invention, the therapeutically effective dose, as described above, of the Compound-meglumine used to treat a patient suffering from DME, is administered to a patient suffering not only from DME but also with diabetic retinopathy (DR). In other embodiments, the DME patient is suffering not only from DME, but also from nonproliferative DR. In other embodiments, the DME patient is also suffering from proliferative DR.

In some embodiments of the claimed invention, the therapeutically effective dose, as described above, of the Compound-meglumine used to treat a patient suffering from AMD. Specifically, said AMD patient may suffer from dry AMD or GA. Specifically, said AMD patient may suffer from wet AMD or nAMD. In other embodiments of the claimed invention, the AMD patient who is treated with a therapeutically effective dose, as described above, of the Compound-meglumine, has a baseline best corrected visual acuity (BCVA) between 70 to 20 Early Treatment Diabetic Retinopathy Study (ETDRS) letters or a baseline 20/40 to 20/400 on the Snellen chart prior to treatment.

In some embodiments of the claimed invention, the DME, DR or AMD patient who is treated with a therapeutically effective dose, as described above, of the Compound-meglumine, has been previously treated with an anti-vascular endothelial growth factor (anti-VEGF) treatment prior to treatment with the claimed invention. In other embodiments, as described herein, the previous treatment with an anti-VEGF treatment occurred in the preceding 6-month period prior to treatment with the methods of the claimed invention. In other embodiments, in addition to having previous treatment with an anti-VEGF treatment, the DME, DR or AMD patient has also presented with a central subfield thickness (CST) of 350 um as measured by SD-OCT at baseline prior to treatment with the methods of the claimed invention.

In some embodiments of the claimed invention, the DME, DR or AMD patient who is treated with a therapeutically effective dose, as described above, of the Compound-meglumine, has, 3 months prior to treatment, a hemoglobin A1C (HbA1C) of <12% at baseline, of <11% at baseline, of <10% at baseline, of <9% at baseline, of <8% at baseline, of <7% at baseline, of <6% at baseline, of <5% at baseline, of <4% at baseline, of <3% at baseline, of <2% at baseline, of <1% at baseline, prior to treatment with the methods of the claimed invention.

In some embodiments of the claimed invention, the DME, DR or AMD patient who is treated with a therapeutically effective dose, as described above, of the Compound-meglumine, has an intraocular pressure (IOP) of ≤23 mmHg at baseline, of ≤22 mmHg at baseline, of ≤21 mmHg at baseline, of ≤20 mmHg at baseline, of ≤19 mmHg at baseline, of ≤18 mmHg at baseline, of ≤17 mmHg at baseline, of ≤16 mmHg at baseline, of ≤15 mmHg at baseline, of ≤14 mmHg at baseline, of ≤13 mmHg at baseline, of ≤12 mmHg at baseline, of ≤11 mmHg at baseline, of ≤10 mmHg at baseline, of ≤9 mmHg at baseline, of ≤8 mmHg at baseline, of ≤7 mmHg at baseline, of ≤6 mmHg at baseline, of ≤5 mmHg at baseline, of ≤4 mmHg at baseline, of ≤3 mmHg at baseline, of ≤2 mmHg at baseline, of ≤1 mmHg at baseline, prior to treatment with the methods of the claimed invention.

In some embodiments of the claimed invention, the DME, DR or AMD patient who is treated with a therapeutically effective dose, as described above, of the Compound-meglumine, the patient has presented with a central subfield thickness (CST) of ≤100 μm as measured by SD-OCT at baseline, of ≤150 μm as measured by SD-OCT at baseline, of ≤200 μm as measured by SD-OCT at baseline, of ≤250 μm as measured by SD-OCT at baseline, of ≤300 μm as measured by SD-OCT at baseline, of ≤350 μm as measured by SD-OCT at baseline, prior to treatment with the methods of the claimed invention.

Administration: Intravitreal (IVT) is a route of administration of a drug, such as the Compound-meglumine described herein, in a procedure to place a medication directly into the space in the back of the eye called the vitreous cavity, which is filled with a jelly-like fluid called the vitreous humor gel. The procedure is usually performed by a trained retina specialist in the office setting. In some embodiments of the claimed invention, the therapeutically effective dose of the Compound-meglumine used to treat DME, DR or AMD, as described above, is administered intravitreally into the patient's eye. In other embodiments, the therapeutically effective dose of the Compound-meglumine used to treat DME, DR or AMD, as described above, is administered into the patient's eye as a single IVT dose.

In some embodiments of the claimed invention, the Compound-meglumine, as described above, is administered intravitreally into the DME, DR or AMD patient's eye first as a loading dose, prior to administering the therapeutically effective dose, as described above. In such a case, the loading dose of the Compound-meglumine, as described above, used to treat a DME, DR or AMD patient is about 0.5 μg per eye, about 1 μg per eye, about 2 μg per eye, about 2.5 μg per eye, about 3 μg per eye, about 4 μg per eye, about 5 μg per eye, about 6 μg per eye, about 7 μg per eye, about 8 μg per eye, about 9 μg per eye, about 10 μg per eye, about 11 μg per eye, about 12 μg per eye, about 13 μg per eye, about 14 μg per eye, about 15 μg per eye, about 16 μg per eye, about 17 per eye, about 18 μg per eye, about 19 μg per eye, about 20 μg per eye, about 21 μg per eye, about 22 μg per eye, about 23 μg per eye, about 24 μg per eye or about 25 μg per eye. In other embodiments, the loading dose of the Compound-meglumine as described above, is in a total volume of 50 μl per eye.

In yet other embodiments of the claimed invention, the Compound-meglumine, as described above, is administered intravitreally into the DME, DR or AMD patient's eye first as a loading dose, prior to administering the therapeutically effective dose, as described above. In such a case, the loading dose of the Compound-meglumine, as described above, used to treat a DME, DR or AMD patient is between 0.5-2 μg per eye, is between 2-4 μg per eye, is between 3-5 μg per eye, is between 4-6 μg per eye, is between 5-7 μg per eye, is between 6-8 μg per eye, is between 7-9 μg per eye, is between 8-10 μg per eye, is between 10-15 μg per eye, is between 15-20 μg per eye, is between 20-25 μg per eye. In other embodiments, the loading dose of the Compound-meglumine as described herein, is in a total volume of 50 μl per eye.

In some embodiments of the claimed invention, the Compound-meglumine, as described above, is administered intravitreally into the DME, DR or AMD patient's eye first as a loading dose, prior to administering the therapeutically effective dose, as described below. In such a case, the loading dose is administered intravitreally into the DME, DR or AMD patient's eye one monthly IVT injection for 2 months, or one monthly IVT injection for 3 months, or at least one IVT injection over 2 months, or at least two IVT injections over 2 months, or at least three IVT injections over 2 months, or at least three IVT injections over 3 months, or at least two IVT injections over 3 months. In other embodiments of the claimed invention, the Compound-meglumine, as described above, is administered intravitreally into the DME, DR or AMD patient's eye first as a loading dose prior to administering the therapeutically effective dose, as described below, and then a gap of treatment is imposed of at least 2 months, of at least 3 months, of at least 4 months, of at least 5 months, of at least 6 months, of at least 7 months, of at least 8 months, of at least 9 months, of at least 10 months, of at least 11 months, of at least 12 months, before administering the therapeutically effective dose, described below.

In some embodiments of the claimed invention, the therapeutically effective dose of the Compound-meglumine, as described above, is administered intravitreally into the DME, DR or AMD patient's eye every 2 months, every 3 months, every 4 months, every 5 months, every 6 months, every 7 months, every 8 months, every 9 months, every 10 months, every 11 months, every 12 months. In other embodiments, the therapeutically effective dose of the Compound-meglumine, as described above, is administered intravitreally into the DME, DR or AMD patient's eye between every 2-3 months, between every 3-4 months, between every 5-6 months, between every 6-7 months, between every 8-9 months, between every 9-10 months, between every 11-12 months. In other embodiments of the claimed invention, the therapeutically effective dose of the Compound-meglumine, as described above, is administered intravitreally into the DME, DR or AMD patient's eye as a single dose every 2 months, a single dose every 3 months, a single dose every 4 months, a single dose every 5 months, a single dose every 6 months, a single dose every 7 months, a single dose every 8 months, a single dose every 9 months, a single dose every 10 months, a single dose every 11 months, or a single dose every 12 months. In other embodiments, the therapeutically effective dose of the Compound-meglumine, as described above, is administered intravitreally into the DME, DR or AMD patient's eye as a single dose between every 2-3 months, as a single dose between every 3-4 months, as a single dose between every 5-6 months, as a single dose between every 6-7 months, as a single dose between every 8-9 months, as a single dose between every 9-10 months, as a single dose between every 11-12 months.

In other embodiments, the therapeutically effective dose of the Compound-meglumine, as described above, is administered intravitreally into the DME, DR or AMD patient's eye once as a single dose, either in conjunction with a prior loading dose as described above, or without one.

Efficacy: In some embodiments the methods of the claimed invention described herein results in the DME, DR or AMD patient demonstrating a CST reduction, as measured by SD-CST of: at least 40 µm from baseline, after being treated with the methods of the invention, at least 50 µm from baseline, after being treated with the methods of the invention, at least 60 µm from baseline, after being treated with the methods of the invention, at least 70 µm from baseline, after being treated with the methods of the invention, at least 80 µm from baseline, after being treated with the methods of the invention, at least 90 µm from baseline, after being treated with the methods of the invention.

In other embodiments the methods of the claimed invention described herein results in the DME, DR or AMD patient demonstrating an absence of macular fluid as assessed by SD-OCT as compared to baseline, after being treated with the methods of the invention.

In some embodiments the methods of the claimed invention described herein results in the DME, DR or AMD patient not requiring more than 2 anti-VEGF treatment rescue, or not requiring more than 3 anti-VEGF treatment rescue, or not requiring more than 4 anti-VEGF treatment rescue, or not requiring more than 5 anti-VEGF treatment rescue. In still other embodiments the methods of the claimed invention described herein results in the patient not requiring any anti-VEGF treatment rescue at all.

In some embodiments the methods of the claimed invention described herein results in the DME, DR or AMD patient demonstrating an improvement in at least 5 ETDRS letter improvement on BCVA over baseline, or at least 6 ETDRS letter improvement on BCVA over baseline, or at least 7 ETDRS letter improvement on BCVA over baseline, or at least 8 ETDRS letter improvement on BCVA over baseline, or at least 9 ETDRS letter improvement on BCVA over baseline, or at least 10 ETDRS letter improvement on BCVA over baseline, or at least 15 ETDRS letter improvement on BCVA over baseline, or at least 20 ETDRS letter improvement on BCVA over baseline. In other embodiments the methods of the claimed invention described herein results in the DME, DR or AMD patient demonstrating an improvement of between 5-7 ETDRS letter improvement on BCVA over baseline, of between 6-8 ETDRS letter improvement on BCVA over baseline, of between 7-9 ETDRS letter improvement on BCVA over baseline, 10-15 ETDRS letter improvement on BCVA over baseline, of between 15-20 ETDRS letter improvement on BCVA over baseline, of between 20-25 ETDRS letter improvement on BCVA over baseline, of between 25-30 ETDRS letter improvement on BCVA over baseline.

In some embodiments the methods of the claimed invention described herein results in the DME, DR or AMD patient demonstrating at least a 0.10 $mm^2$ reduction of ocular avascular area over baseline, or at least a 0.20 $mm^2$ reduction of ocular avascular area over baseline, or at least a 0.30 $mm^2$ reduction of ocular avascular area over baseline, or at least a 0.40 $mm^2$ reduction of ocular avascular area over baseline, or at least a 0.50 $mm^2$ reduction of ocular avascular area over baseline, or at least a 0.60 $mm^2$ reduction of ocular avascular area over baseline, or at least a 0.70 $mm^2$ reduction of ocular avascular area over baseline, or at least a 0.80 $mm^2$ reduction of ocular avascular area over baseline, or at least a 0.90 $mm^2$ reduction of ocular avascular area over baseline, or at least a 1.0 $mm^2$ reduction of ocular avascular area over baseline, all as measured by fluorescence angiography (FA) or optical coherence tomography angiography (OCT-A).

In other embodiments the methods of the claimed invention described herein results in the DME, DR or AMD patient having a 2-step improvement in diabetic retinopathy severity scale (DRSS) over baseline.

In still other embodiments the methods of the claimed invention described herein results in the DME, DR or AMD patient demonstrates a regression in neovascularization over baseline, as measured, for example, by FA or OCT-A.

EXAMPLES

The following are examples of methods and compositions of the invention. It is understood that various other embodiments may be practiced, given the general description provided above.

Example 1: Assessment of Safety and Tolerability Study of the Compound of Formula I in Patients With Diabetic Macular Edema or Neovascular Age-Related Macular Degeneration This is a Phase 1, open-label, first-in-human (FIH), single-ascending dose (SAD) study consisting of approximately 4 cohorts. The total number of patients was at least 3 per cohort plus 3 additional patients in the maximum tolerated dose (MTD) cohort. The compound of Formula I was administered intravitreally and all patients were followed for approximately 6 months.

The rationale to enroll patients with DME in the first-in-human study is based on the fact that an IVT injection is an invasive procedure that is not risk-free. As with other IVT injected drugs approved by FDA, this trial enrolled patients with DME to establish the pharmacology, safety and preliminary effectiveness of the drug in the diseased population because of the potential risk presented by the IVT injection. Single dose toxicity has been studied using the proposed route of administration in the target population. In addition, this was designed to determine the safety profile of different doses and determine if there are any dose limiting toxicity (DLTs).

Patients enrolled in the FIH study were those diagnosed as having DME (as defined by the AAO PPP DME Guidelines [2019]) with BCVA in the study eye of 35 ETDRS letters or worse (equivalent to 20/200 on the Snellen chart) and have vision in the non-study eye that is of better acuity than 35 ETDRS letters (20/200 on the Snellen chart). Patients enrolled could also have nonproliferative diabetic retinopathy (NPDR) with DME who, in the opinion of the investigator, were unlikely to benefit from or failed current treatment options, such that no significant additional harm is expected. Other inclusion and exclusion criteria ensure that those enrolled have no retinal disease other than DME that can compromise BCVA, prevent BCVA improvement, require medical or surgical intervention during the study period, confound interpretation of the results, or interfere with assessment of toxicity of ophthalmological assessments in the study eye. Enrolled patients were not chosen to have any conditions, including laboratory findings and findings in medical history or in the pre-study assessments that, in the opinion of the investigator, constituted a risk or contraindication for participation in the study or that could interfere with the study objectives, conduct, or evaluation or prevent the patient from fully participating in all aspects of the study.

The escalation from a single dose of 0.5 µg, 1.0 µg, 2.5 µg or 5.0 µg of the compound of Formula I in a 50 µL injection volume was designed to limit FIH exposure to a dose with a >5-fold margin over the PAD of the compound of Formula I in mice and not to exceed a >2-fold safety margin over the NOAEL. The design allowed for detection of unexpected acute toxicities in a sentinel patient followed by close review of all available data by the safety assessment committee (SAC) prior to adding additional patients to a dose group. See FIG. 1.

Inclusion Criteria:
Nonproliferative diabetic retinopathy (DR) patients with DME or patients with nAMD.
Center-involved DME with central subfield thickness (CST) 350 μm on SD-OCT and for nAMD, active choroidal neovascularization (CNV) associated with age-related macular degeneration as evidenced on FA and SD-OCT at Day 1, including presence of intraretinal or subretinal fluid.
BCVA in the study eye (most affected) of 55 Early Treatment Diabetic Retinopathy Study (ETDRS) letters or worse screening and on Day 1.
Patients who have the capacity to give informed consent and who are willing and able to comply with all study-related procedures and assessments.

Exclusion Criteria:
Any ocular/intraocular/periocular infection or inflammation in either eye.
History of vitreous hemorrhage in the study eye within 2 months prior to screening and subretinal hemorrhage with bleeding area disc area in the study eye.
Any retinovascular disease or retinal degeneration other than DME or nAMD in the study eye.
History of systemic and intraocular steroid use for 6 months prior to Day 1. The use of intravitreal nonbiodegradable steroid implants (ex. Iluvien®, Yutiq®, Retisert®) is prohibited.
Significant media opacities, including cataract, which might interfere with VA, assessment of toxicity, or fundus imaging.
Any uncontrolled medical condition that, in the opinion of the investigator, would preclude participation in this study.

Upon conclusion of the Phase I study, the data demonstrated that no adverse events attributed to the compound of Formula I were demonstrated at any of the doses studied. Up to 10 μg of the compound of Formula I was well tolerated with a favorable safety profile through 24 wks. No dose-limiting toxicities were observed with no evidence of acute inflammation, infection, increase in IOP, or hemorrhage. A total of two nonserious, nondrug-related AEs were reported.

Figure 3:
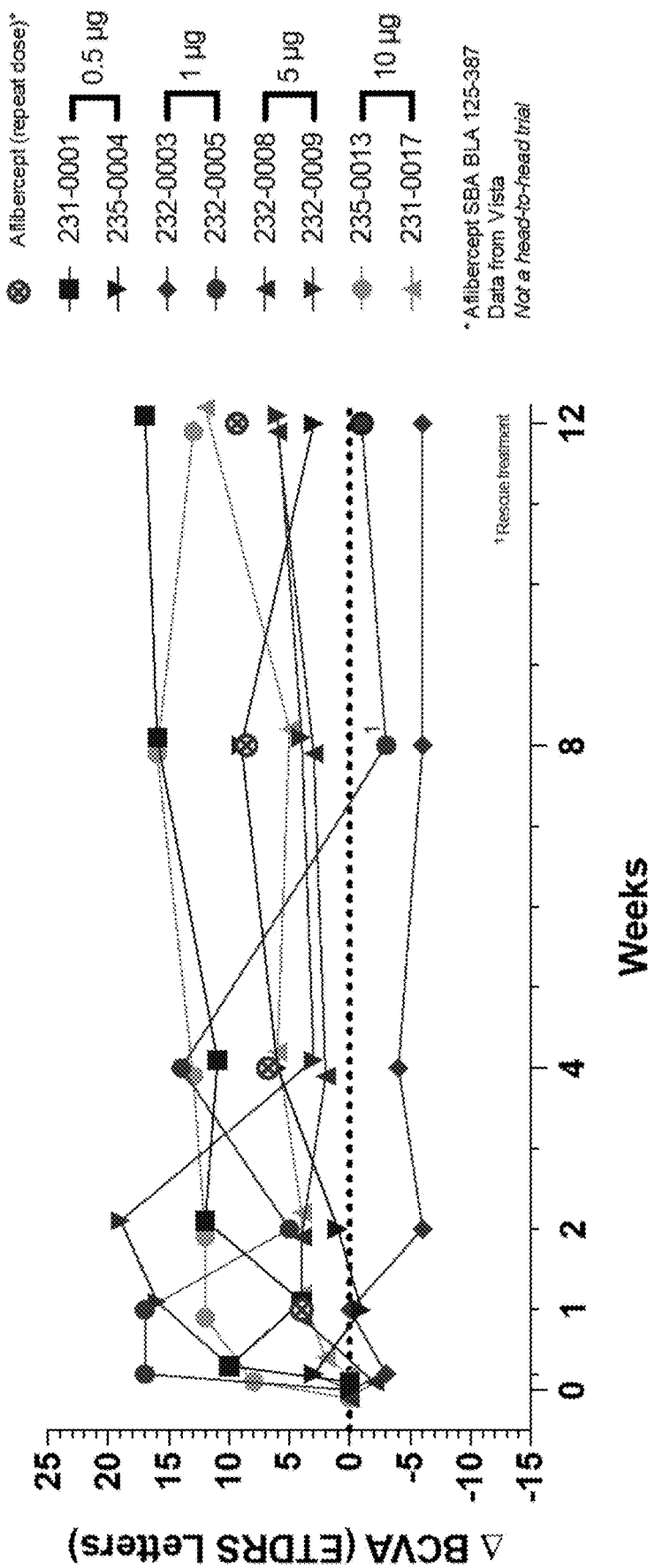
FIG. 3 shows the BCVA change from baseline for DME patients as a result of the Phase I study described in Example 1. Note that the aflibercept data, taken from the published VISTA study, is superimposed on the data for comparison purposes only. At all doses studied, 6 of 8 patients showed a gain in ETDRS letters from baseline at 2 weeks. At 4 weeks, 7 of 8 patients showed a gain in ETDRS letters from baseline and at 12 weeks, 6 of 8 patients showed a gain in ETDRS letters from baseline.
Figure 4:
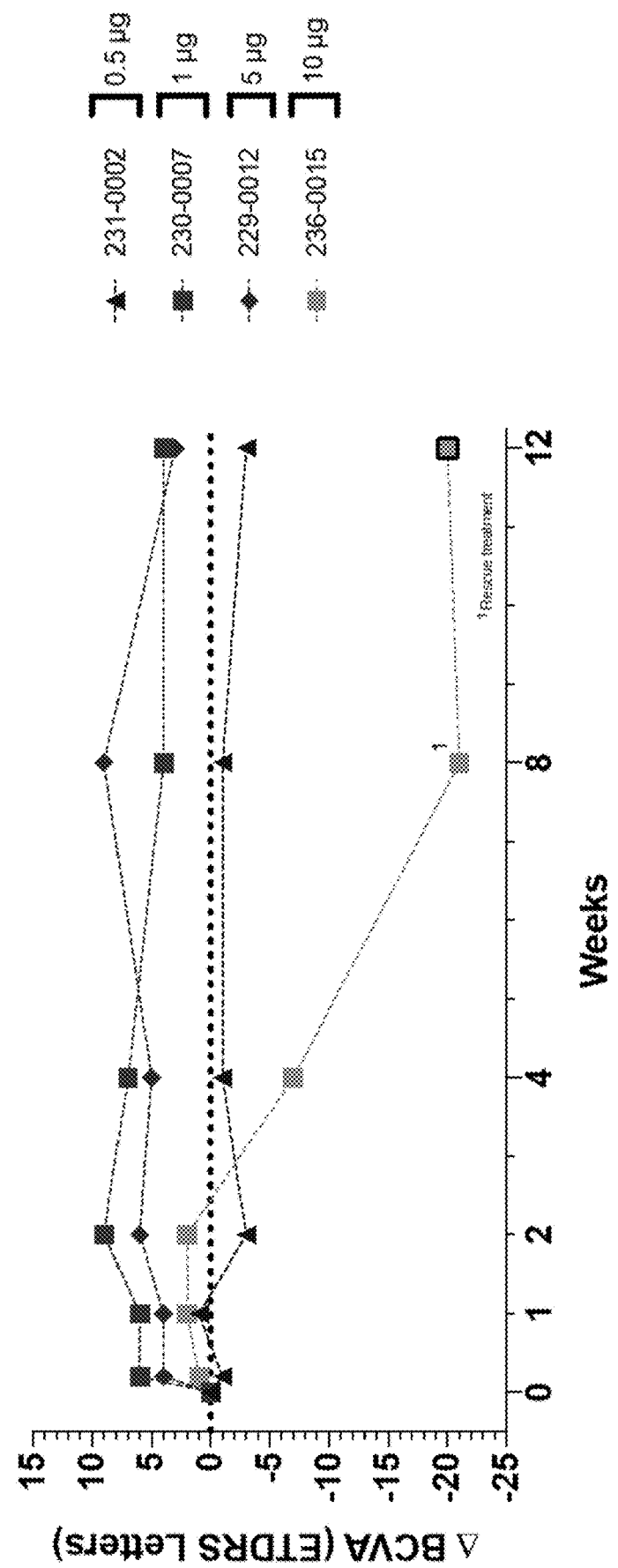
FIG. 4 shows the BCVA change from baseline for nAMD patients as a result of the Phase I study described in Example 1. At all doses studied, 3 of 4 patients showed a gain in ETDRS letters from baseline at 2 weeks, while 2 of 4 patients demonstrated an ETDRS letter gain from baseline at 4 weeks. At 12 weeks, 2 of 4 patients demonstrated an ETDRS letter gain from baseline. Note that one patient was administered an anti-VEGF rescue treatment.
Figure 8:
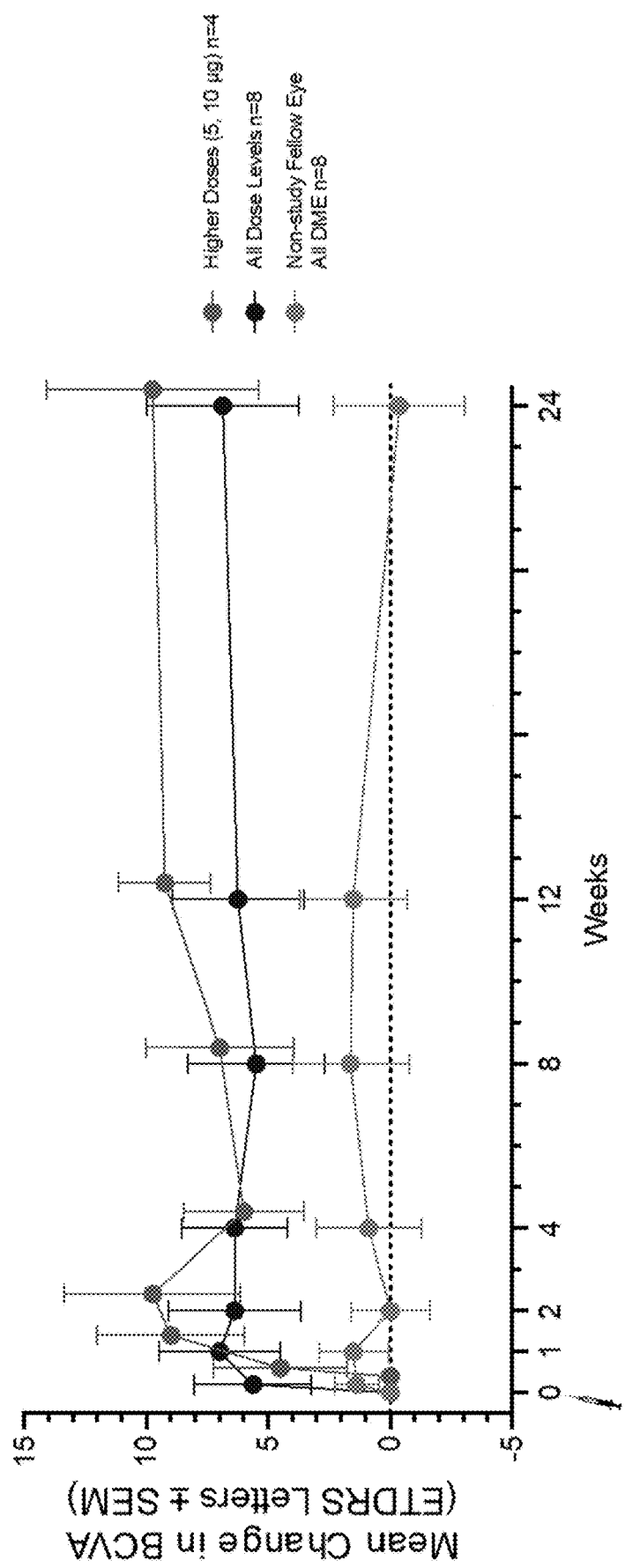
FIG. 8 shows the mean change in BCVA in patients with DME through 24 weeks as a result of a single injection of the compound of formula I as described in the Phase I study disclosed in Example 1.
Figure 9:
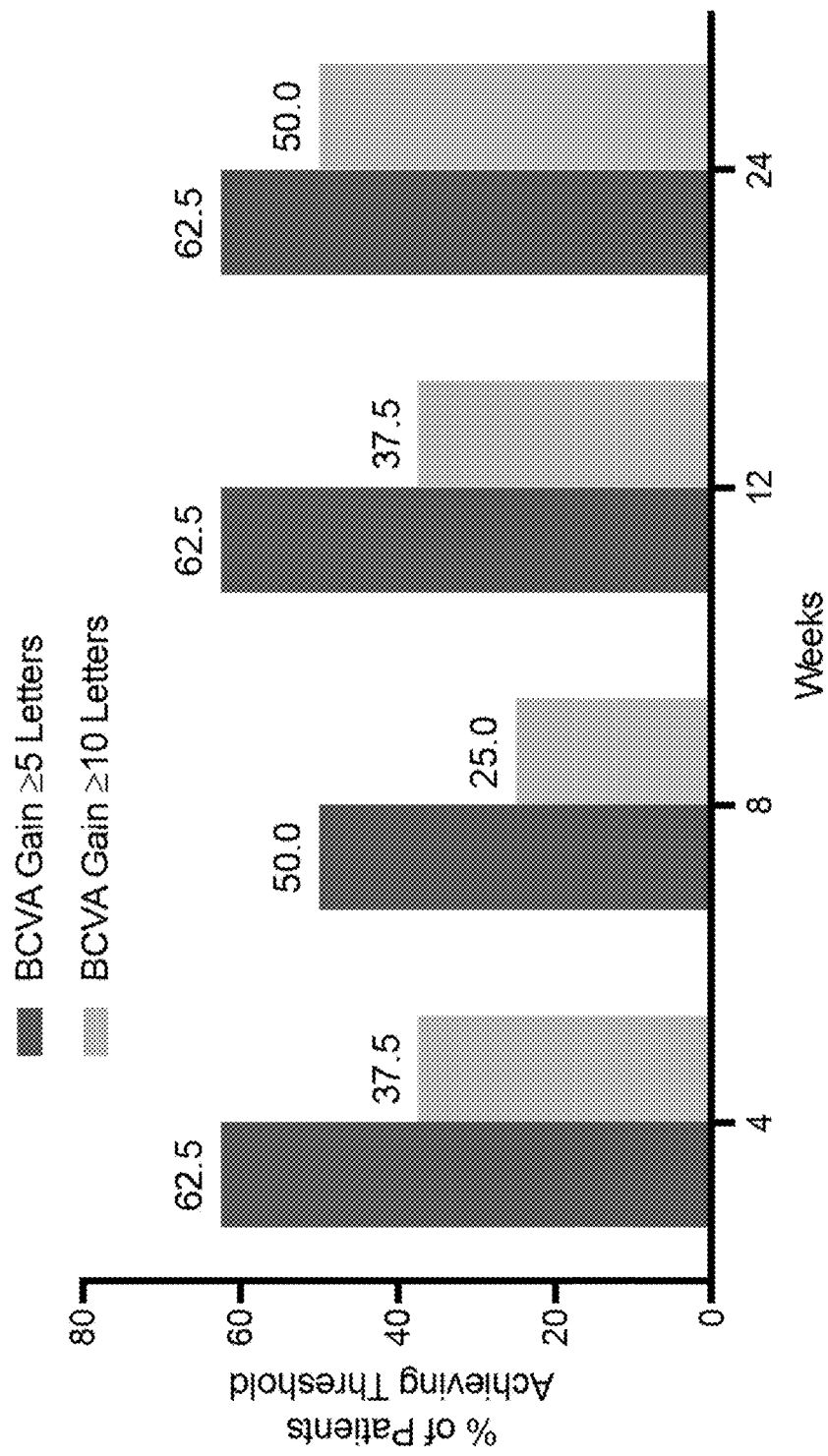
FIG. 9 depicts the percent of DME patients achieving a threshold BCVA gain of either equal to or greater than 5 letters or BCVA gains of equal to or greater than 10 letters after a single injection of the compound of formula I as measured at 4 weeks, 8 weeks, 12 weeks and 24 weeks, in the Phase I study described in Example 1.

Overall, at all doses studied, 10 of 12 DME and nAMD patients in the study showed a gain in ETDRS letters from baseline at 2 weeks, as well 9 of 12 patients at 4 weeks. At 12 weeks, 8 of 12 DME and nAMD patients showed a gain in ETDRS letters from baseline. At the higher dose cohorts of 5 ug and 10 ug, 6 of 6 patients showed a gain in ETDRS letters from baseline at 2 weeks, and 5 of 6 patients at 4, 8 and 12 weeks. See FIG. 3 for DME patients and FIG. 4 for nAMD patients. At 24 weeks, 8 out of 12 DME patients showed a sustained gain in ETDRS letters as measured by the mean change in BCVA. See FIG. 8. This sustained BCVA gain after a single injection of the Compound of Formula I is also graphically shown in FIG. 9 as assessed at 4 weeks, 8 weeks, 12 weeks and 24 weeks.

Figure 12:
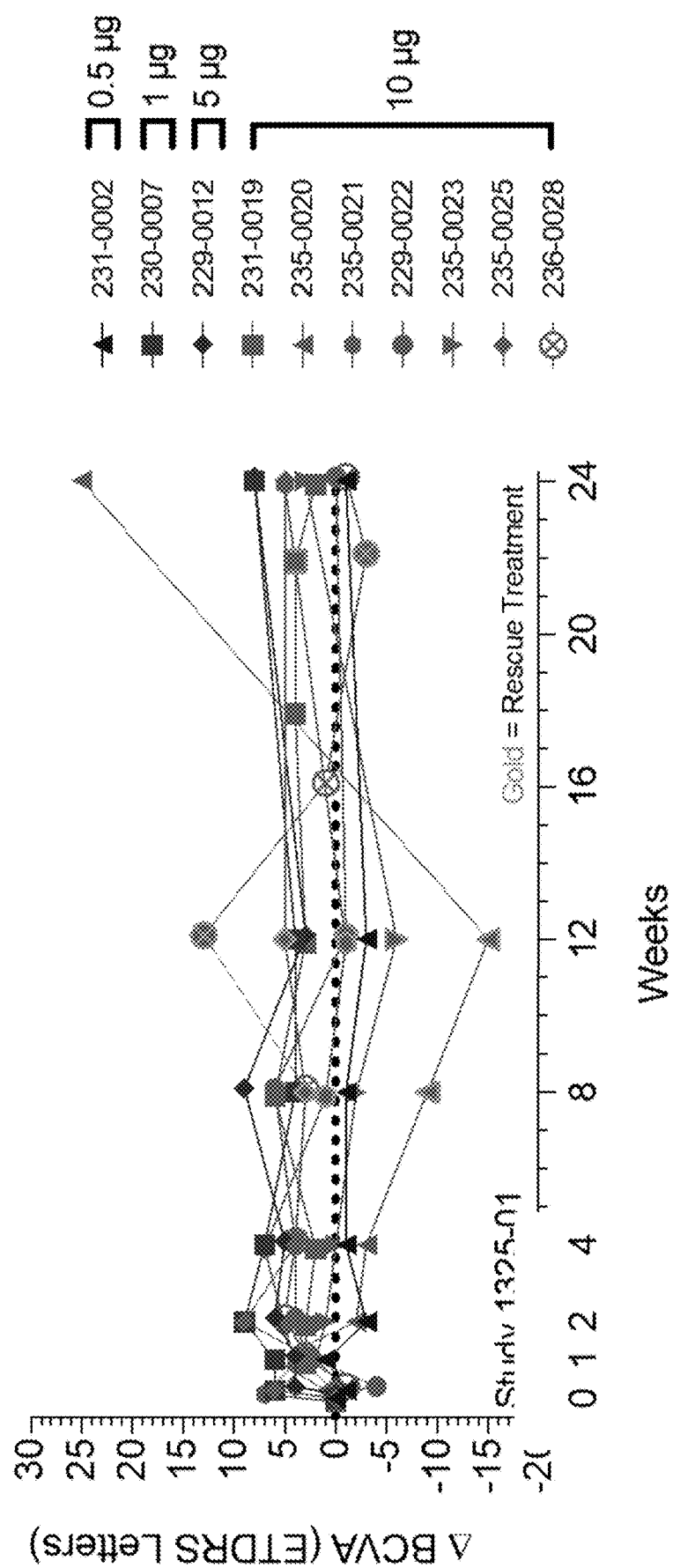
FIG. 12 shows the individual AMD patient plot change in BCVA as measured by ETDRS in 10 patients at all doses tested. Five patients were given anti-VEGF rescue treatment, as indicated by the "Gold" outline. See Example 1.
Figure 13:
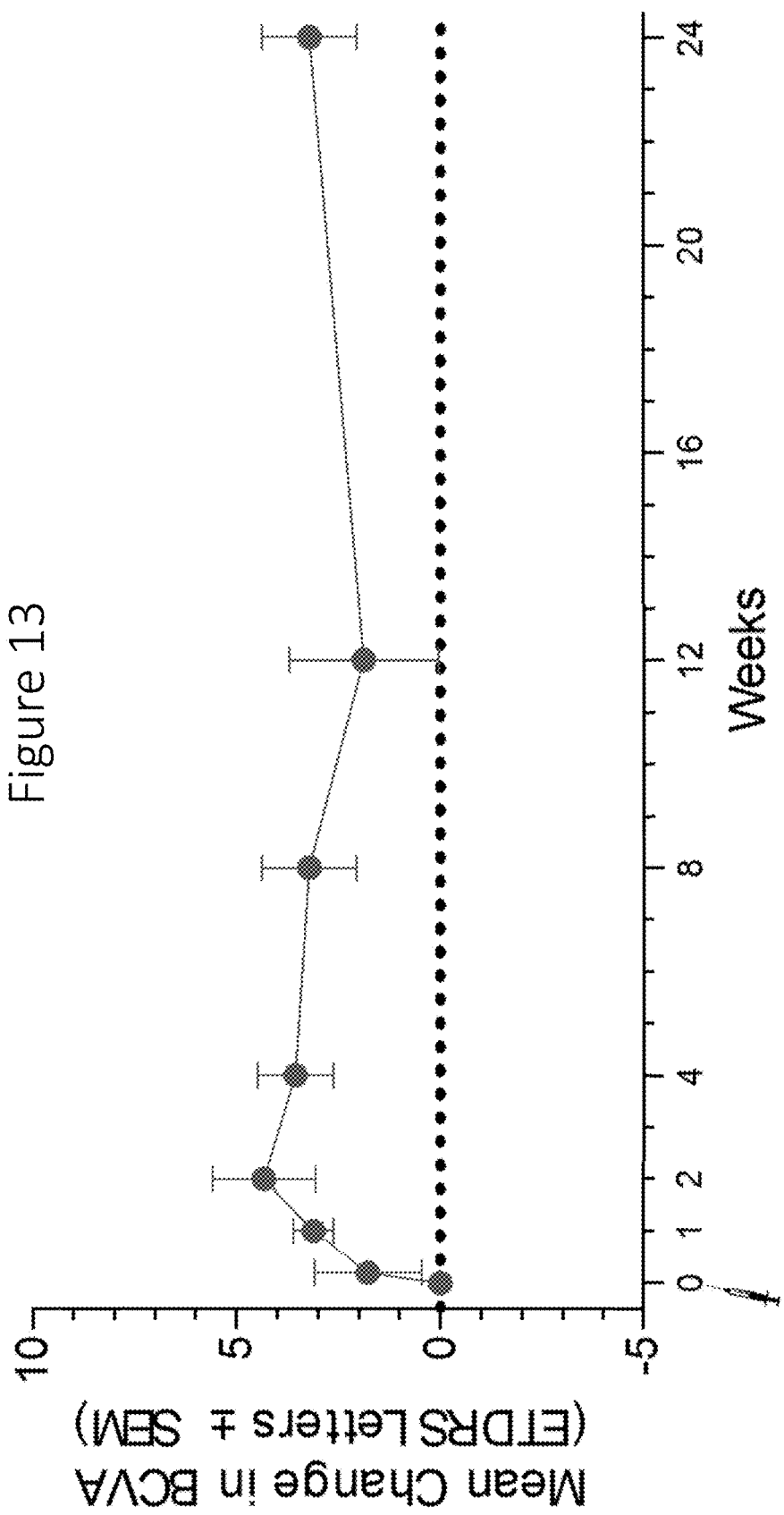
FIG. 13 shows an Intent-to-Treat (ITT) analysis of the mean change in BCVA in 9 AMD patients where 6 AMD patients received an anti-VEGF rescue treatment and 3 did not, as measured by ETDRS letters±SEM at 1 week, 2 weeks, 4 weeks, 8 weeks, 12 weeks and 24 weeks after a single injection of the compound of formula I. See Example 1.

In AMD patients tested, after a single injection of the Compound of Formula I, a rapid improvement in BCVA was observed and appeared to either improve or stabilize through six months post-injection. See FIGS. 12 and 13. Among the six AMD patients who received an anti-VEGF rescue treatment, there were minimal changes in either mean BCVA, see FIGS. 12 and 13. It is noted that in FIG. 13, the Intent-to-Treat (ITT) analysis excluded one patient, 235-0020 who received an anti-VEGF rescue treatment, and whose individual plot is shown in FIG. 12.

Figure 5:
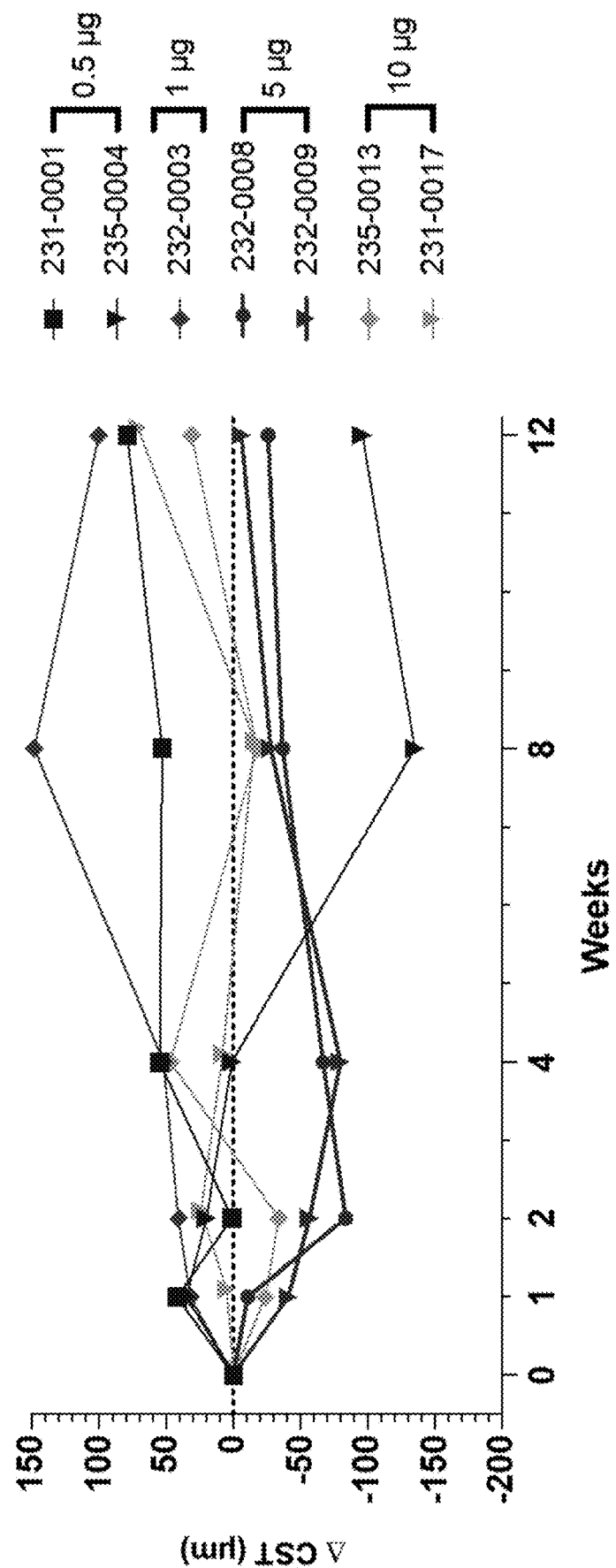
FIG. 5 shows the CST change from baseline for DME patients as a result of the Phase I study described in Example 1. At all doses studied, 3 of 7 patients had a decrease in CST from baseline at 2 weeks, and 2 of 7 patients showed a decrease from baseline at 4 weeks. At 12 weeks, 4 of 7 patients showed a decrease from baseline.
Figure 6:
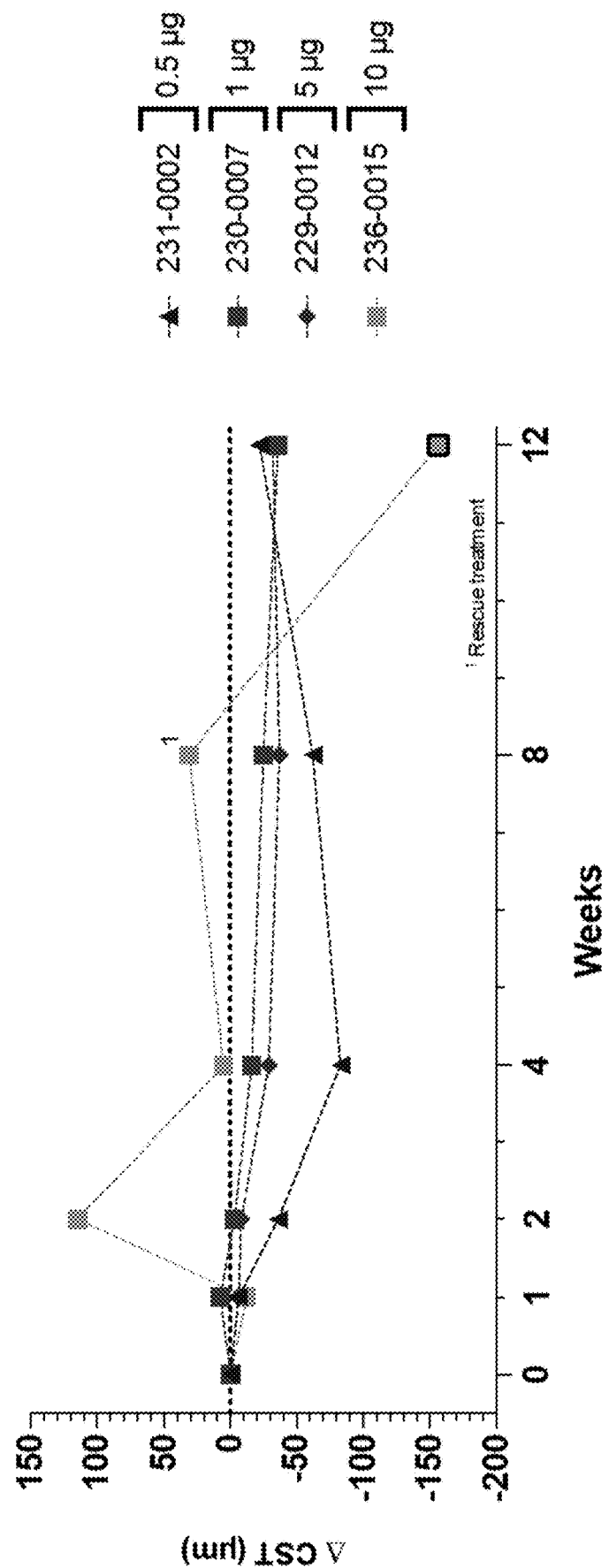
FIG. 6 shows the CST change from baseline for nAMD patients as a result of the Phase I study described in Example 1. At all doses studied, 2 of 4 patients had a decrease in CST from baseline at 2 weeks, and 3 of 4 patients showed a decrease from baseline at 4 weeks. At 12 weeks, 3 of 4 patients showed a decrease from baseline. Note that one patient was administered an anti-VEGF rescue treatment.
Figure 11:
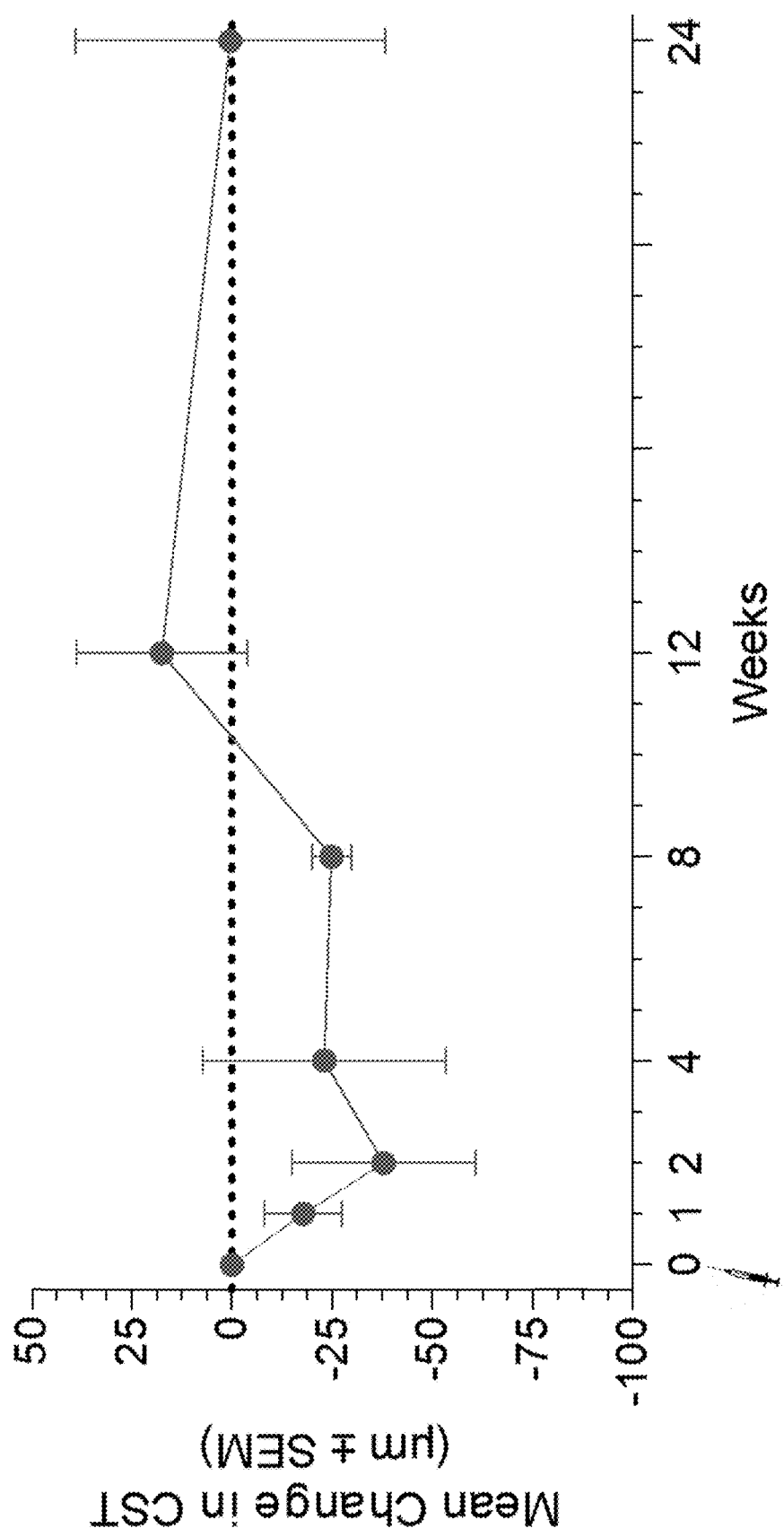
FIG. 11 shows the mean change in CST in the high dose cohort of 8 DME patients after receiving a single injection of the compound of formula I as followed out to 24 weeks. See Example 1.
Figure 14:
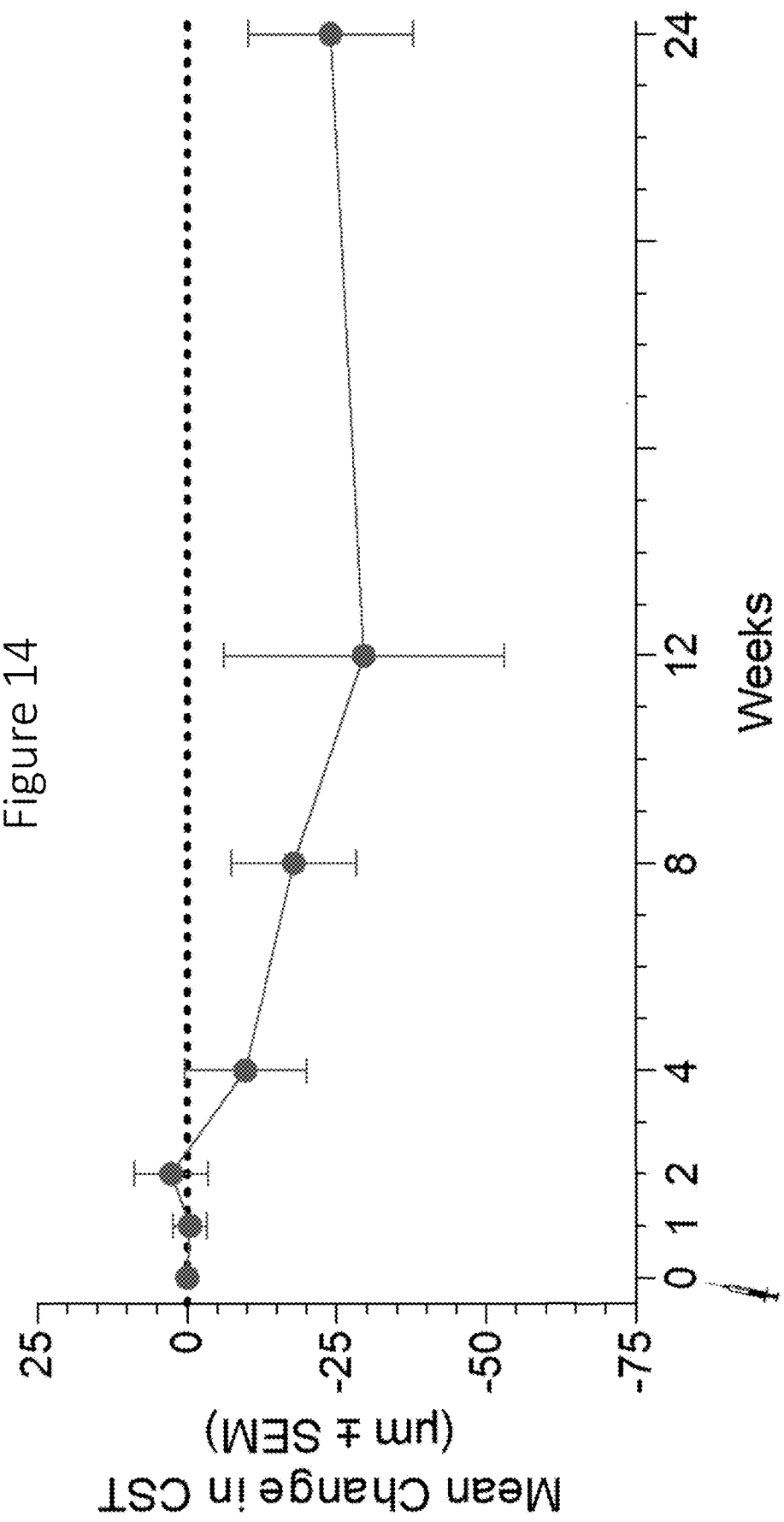
FIG. 14 shows an Intent-to-Treat (ITT) analysis of the mean change in CST as measured by µm±SEM in 10 AMD patients at 1 week, 2 weeks, 4 weeks, 8 weeks, 12 weeks and 24 weeks after a single injection of the compound of formula I. See Example 1.

Further, at all doses studied, 6 of 12 DME and nAMD patients in the study demonstrated a decrease in CST from baseline at 2 weeks, and 5 of 12 patients showed a decrease at 4 weeks and 8 of 12 patients showed a decrease at 8 weeks and 5 of 10 patients showed a decrease at 12 weeks. At the higher dose cohorts of 5 and 10 ug, 4 of 6 patients showed a decrease in CST from baseline at 2 weeks and 3 of 6 patients at 4 weeks, 5 of 6 patients showed a decrease in CST at 8 weeks and 3 of 5 patients at 12 weeks. See FIG. 5 for DME patients and FIG. 6 for nAMD patients. At 24 weeks, 8 DME patients at the higher dose cohort showed a mean CST that appeared to settle back to baseline. See FIG. 11. In 9 AMD patients analyzed, which included those six who received anti-VEGF rescue and three who did not, there were minimal changes in mean CST through 24 weeks, see FIG. 14, suggesting that after a single injection of the Compound of Formula I, there were improvements in or stabilization of CST through 24 weeks.

Figure 10:
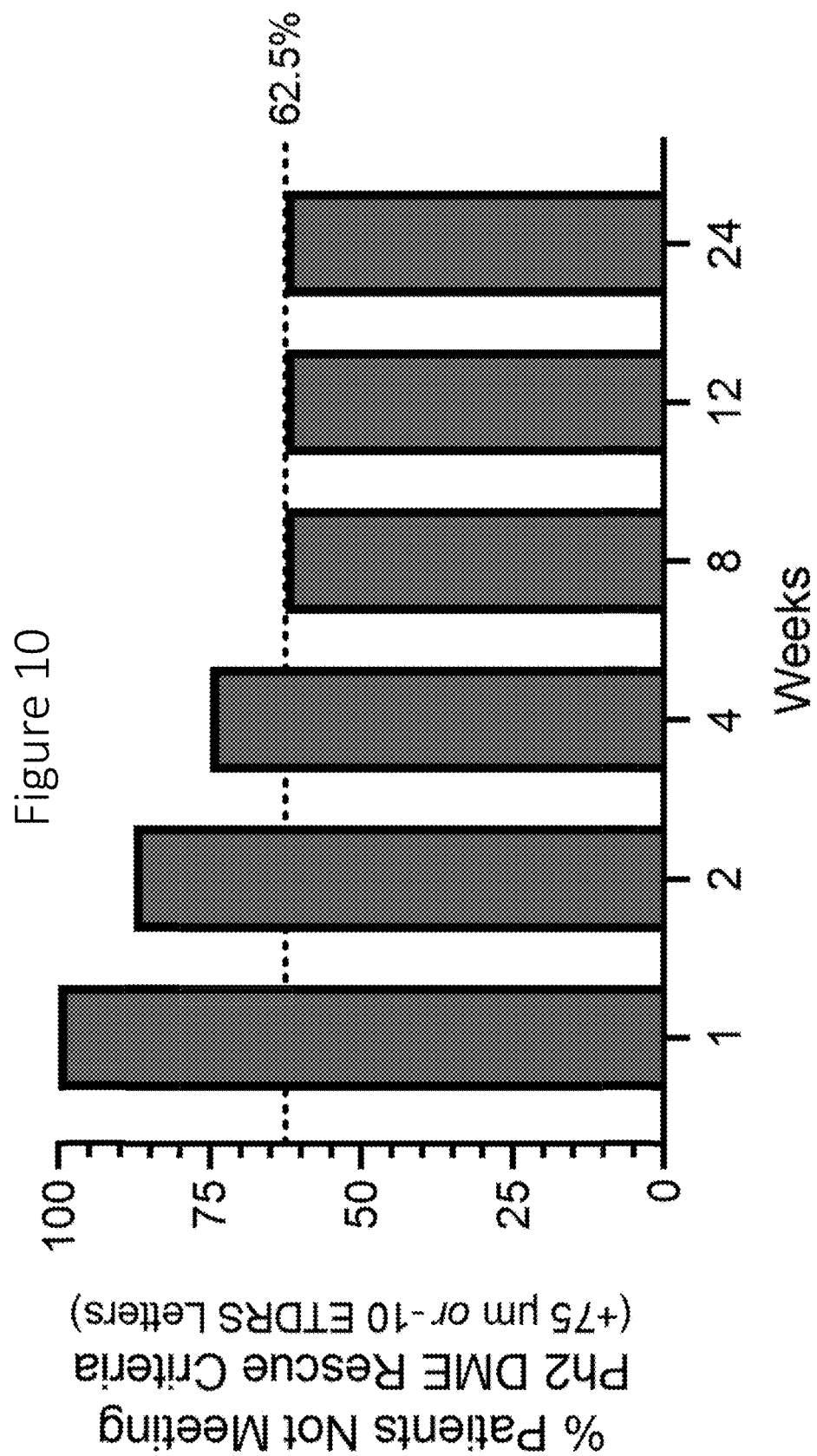
FIG. 10 depicts the percent of DME patients not meeting a Phase 2 DME rescue criteria with an anti-VEGF therapy, which is +75 µm or −10 ETDRS letters in the Phase I study described in Example 1.

Further, FIG. 10 shows that after a single injection of the Compound of Formula I, 62.5% of DME patients in this study did not meet a Phase 2 DME rescue criteria with an anti-VEGF therapy, which is +75 um or −10 ETDRS letters, through six months.

Through 12 wks and 24 wks, a single IVT injection of the Compound of Formula I of up to 10 μg was safe and well tolerated in patients with advanced DME or nAMD. Disease-relevant biological activity was observed by increased BCVA, reduced CST, intraretinal, and subretinal fluid in this patient population.

Figure 2:
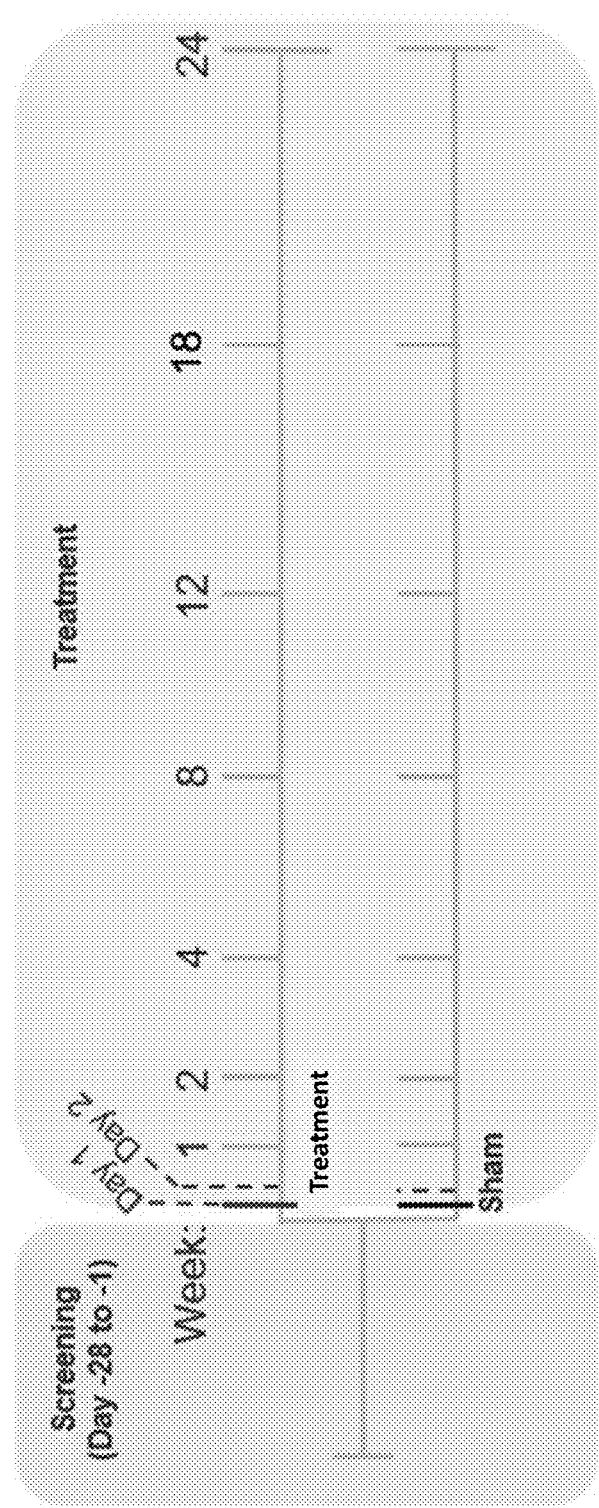
FIG. 2 depicts a schematic of the Phase 2a proof-of-concept study in DME as described in Example 2.

Example 2: Assessment of Safety and Biological Activity Following a Single Intravitreal Injection of the Compound of Formula I in Patients with DME A Phase 2a, Proof-of-Concept (POC), prospective, multicenter, randomized, single masked, sham-controlled study to assess the safety, tolerability and evidence of activity of a single IVT injection of the compound of Formula I in subjects with DME was performed. Approximately 62 total patients will be enrolled 1:1 in the test or sham study arms, in order to assess the primary objective. All patients will be followed for approximately 24 weeks. See FIG. 2.

The primary efficacy endpoint is a change from baseline in CST at Week 24 as assessed by SD-OCT. The SD-OCT image data will be assessed by a reading center. The primary efficacy endpoint will be analyzed by mixed model for repeated measures (MMRM).

Patients will be those diagnosed as having DME (as defined by the AAO PPP DME Guidelines 2019) with BCVA in the study eye of 70 to 20 ETDRS letters (equivalent to 20/40 to 20/400 on the Snellen chart) and have vision in the non-study eye that is of better acuity than 35 ETDRS letters (20/200 on the Snellen chart).

The planned dose of the compound of Formula I is 5 μg and will be escalated to 10 μg pursuant to the favorable safety data in the Phase 1 SAD study described in Example 1.

Inclusion Criteria: To be included in this study, each individual must satisfy all of the following criteria:
1. Patients aged 18 years and older.
2. Nonproliferative DR patients with DME who had at least 3 anti-VEGF treatments in the preceding 6 months prior to Day 1, with the last anti-VEGF given between 3 and 5 weeks prior to Day 1.
3. Center-involved DME with central subfield thickness (CST) ≥350 μm on SD-OCT at Screening.
4. BCVA in the study eye (most affected) of 70 to 20 ETDRS letters (equivalent to 20/40 to 20/400 on the Snellen chart) at Screening and at Day 1. If both eyes are equal, then it is at the Investigator's discretion.
5. BCVA in the non-study eye of 35 ETDRS letters (equivalent to 20/200 on the Snellen chart) or better.
6. IOP≤23 mmHg in the study eye.
7. Clear ocular media and adequate pupillary dilatation to permit CFP and adequate BCVA evaluation.
8. Patients who have the capacity to give informed consent and who are willing and able to comply with all study-related procedures and assessments.

Exclusion Criteria: If an individual meets any of the following criteria, he or she is ineligible for this study:
1. Concurrent disease in the study eye or structural damage, other than DME, that could compromise BCVA, prevent BCVA improvement, require medical or surgical intervention during the study period, confound interpretation of the results, or interfere with assessment of toxicity or CFP in the study eye. This includes, but is not limited to, the following:
   Macular edema of etiologies other than diabetes
   Clinically significant subretinal fibrosis
   Subfoveal lipid
   Cataract requiring surgery during the study period
   RPE atrophy or tear or rips involving the macula
   Clinically significant macular hole
   Clinically significant noninfectious uveitis
   Vitreomacular traction
   Clinically significant epiretinal membrane (ERM)
   Aphakia
   Pseudophakia with anterior chamber intraocular lens (A/C IOL)
2. HbA1c≤12 and/or recent signs of uncontrolled diabetes
3. Any ocular/intraocular/periocular infection or inflammation in either eye in the past 4 weeks prior to Screening (mild blepharitis is acceptable)
4. History of vitreous hemorrhage in the study eye within 2 months prior to Screening
5. History of IVT, subconjunctival, or periocular steroids in the 3 months prior to Screening
6. History of vitrectomy in the study eye
7. History of intraocular, periocular, or corneal surgery in the study eye within 3 months prior to Screening, or anticipated need for such surgery during the study
8. History of panretinal photocoagulation (within 6 months) or macular laser photocoagulation (within 3 months) in the study eye prior to dosing
9. History of corneal transplant in the study eye
10. Concomitant use of >2 medications for the treatment of glaucoma and unstable glaucoma in the study eye (i.e., inadequate IOP control)
11. Any condition, including laboratory findings and findings in the medical history or in the pre-study assessments, that, in the opinion of the Investigator, constitutes a risk or contraindication for participation in the study or that could interfere with the study objectives, conduct, or evaluation or prevent the patient from fully participating in all aspects of the study
12. Presence of severe myopia (−8 diopters or greater) in the study eye
13. History of systemic and intraocular steroid use for 6 months prior to Day 1. The use of intravitreal nonbiodegradable steroid implants (ex. Iluvien®, Yutiq®, Retisert®) is prohibited
14. Significant media opacities, including cataract, which might interfere with visual acuity, assessment of toxicity, or fundus imaging
15. Intraocular surgery, including cataract surgery, in the study eye months of screening
16. Known allergy to dye injected during FA
17. Known allergy to any component (phosphate buffered saline and polysorbate 80) in the Compound of Formula I.
18. Female patients who are pregnant, lactating, or of childbearing potential who do not agree to use highly effective methods of birth control (e.g., progesterone-only hormonal contraception, double barrier, or intrauterine device) during the study and for 3 months following the last dose of Compound of Formula I. Postmenopausal females (>45 years old and without menses for more than 1 year) and surgically sterilized females are exempt from these requirements.
19. Male patients who do not agree to use a highly effective method of contraception during the study and for 3 months following the last dose of Compound of Formula I, if sexually active with a female partner of childbearing potential.
20. Patients who within 3 months of screening received or are concurrently on another investigational drug or vaccine study, including patients who previously received treatment in a study using the compound of Formula I.
21. Any uncontrolled medical condition, in the opinion of the Investigator, would preclude participation in this study, including, but not limited to, history of malignancy within the last 3 years (however, non-facial, basal cell carcinoma is allowed), history of myocardial infarction within the last 6 months, or concomitant therapy.

The compound of Formula I is administered via IVT injection. Following the IVT injection, patients will be monitored for elevation of IOP, decreased optic nerve head perfusion, and for possible injection complications (e.g., vitreous hemorrhage, retinal tears, etc.). Additionally, patients should immediately report any symptoms suggestive of endophthalmitis, such as ocular pain, swelling, redness, haze and gradual loss of vision.

Control will be a sham procedure (i.e., needleless, empty sterile syringe) touched to the surface of the study eye to mimic an IVT injection. Patients may be prescribed prophylactic antibiotic eye drops following the study or sham procedure per the site's preferred practice patterns and documented.

Permitted Treatments: Permitted concomitant treatments in/for the study eye and sham eye include:
   Topical antibiotics administered prophylactically with IVT injection and topical/systemic antibiotics used for AE treatment.
   Artificial tears
   Steroid use is permitted only for the following conditions:
      Topical (e.g., for atopic dermatitis treatment), inhaled (e.g., for asthma treatment), or locally injected (e.g., for epidural or joint injection)
      Topical use of steroids in the fellow eye
      Topical use of steroids for treatment of inflammation in the study eye (e.g., uveitis).

Concomitant intravitreal therapy in the fellow eye is permitted but cannot be administered within 7 days of treatment with masked study drug.

Prohibited Treatments: There are no known contraindications to the administration of the compound of Formula I. Patients will not be permitted to received treatments for the management of DME in the study eye, once randomized to this study, unless it is a rescue treatment. Systemic (oral, intramuscular, and intravenous) steroids are not allowed unless for an adverse event (AE) treatment. All systemic steroids should be discontinued before the study drug administration. Patients should not have received any therapy that would preclude an IVT injection. Patients are prohibited from receiving any medication for the study eye that, in the opinion of the Investigator and/or the Medical Monitor, may have an effect on the study results.

Example 3: A Phase 2a Assessment of Safety, Tolerability and Evidence of Activity Following a Single Intravitreal Injection of the Compound of Formula I in Patients with nAMD This is a Phase 2a Proof-of-Concept (POC) study. The total number of patients will be approximately 40 patients who will be enrolled and randomized 1:1 into either the Compound of Formula I or sham study arms, in order to assess the primary objective. All patients will be followed for approximately 16 weeks.

The objective of this Phase 2a study is to assess the local and systemic safety and tolerability following a single IVT injection of Compound of Formula I compared to sham at Week 8 and 16. The primary endpoint of this Phase 2a is to determine the ocular and systemic safety and tolerability of a single IVT injection of Compound of Formula I evaluated by treatment emergent adverse events (TEAEs). The secondary endpoints are to assess the biological activity, efficacy parameters and retinal structure improvements following a single IVT injection of the Compound of Formula I. Specifically, the study will investigate the proportion of patients who require 2 or more anti-VEGF rescue over 8 and 16 weeks, the duration of effect as measured by the time from randomization to receipt of standard of care as determined by the investigator based on rescue criteria, changes in BCVA from baseline to week 8 and week 16, the change in CST from baseline to week 8 and week 16 as assessed by SD-OCT, the change in retinal fluid from baseline to week 8 and week 16 assessed by SD-OCT, and the proportion of patients with absence of exudation: subretinal fluid (SRF), intraretinal fluid (IRF), and/or cystoid edema. A further endpoint is to assess efficacy parameters and retinal structure improvement of patients following a single IVT injection of the Compound of Formula I, which is a change in capillary perfusion from baseline to week 8 and week 16 as assessed by OCT-A and FA, as well as a change in drusen volume from baseline to week 8 and week 16.

Figure 7:
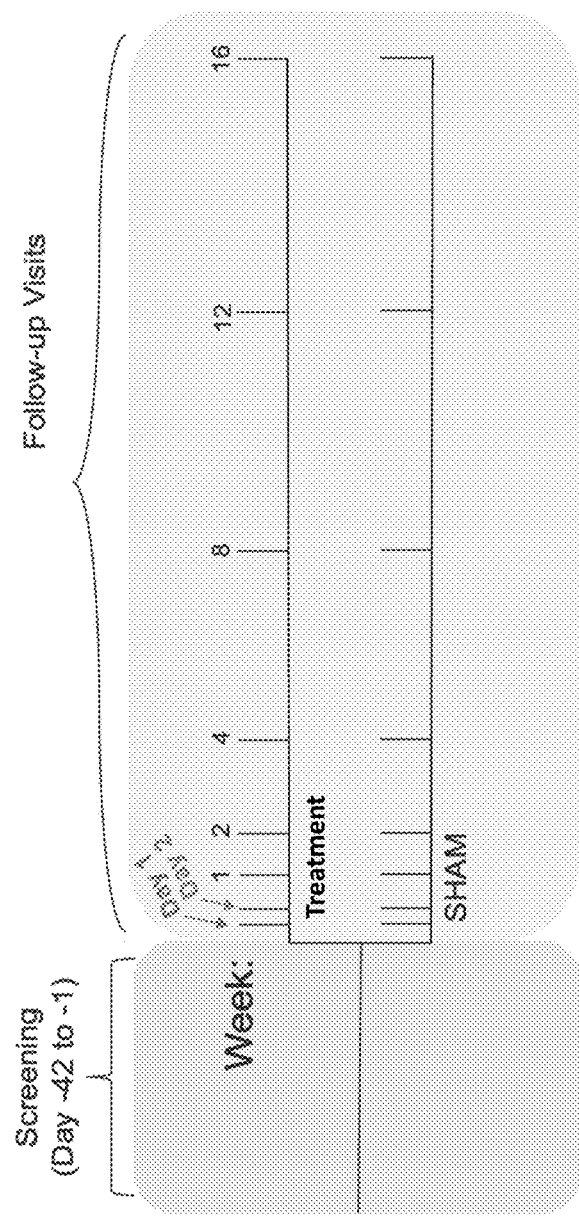
FIG. 7 depicts a schematic of the Phase 2a proof-of-concept study in nAMD as described in Example 3.

This study will enroll patients 50 years of age with nAMD with best corrected visual acuity (BCVA) between 70 to 20 Early Treatment Diabetic Retinopathy Study (ETDRS) letters (equivalent to 20/40 to 20/400 on the Snellen chart) at Screening and at Day 1. Patients will be administered a single 50 µL IVT injection of 10 µg of Compound of Formula I or sham. See FIG. 7.

Inclusion Criteria

To be included in this study, each individual must satisfy all of the following criteria:
1. Patients aged 50 years.
2. Active choroidal neovascularization (CNV) associated with age-related macular degeneration as evidenced on FA and SD-OCT at Day 1 and confirmed by central reading center with presence of intraretinal or subretinal fluid.
3. Neovascular AMD patients who had at least 3 anti-VEGF treatments in the preceding 6 months prior to Day 1, with the last anti-VEGF given between 3 and 6 weeks prior to Day 1.
4. BCVA in the study eye (most affected) of 70 to 20 ETDRS letters (equivalent to 20/40 to 20/400 on the Snellen chart) at Screening and at Day 1. If both eyes are equal, then it's Investigator discretion.
5. BCVA in the non-study eye of 35 ETDRS letters (equivalent to 20/200 on the Snellen chart) or better.
6. IOP≤23 mmHg in the study eye.
7. Clear ocular media and adequate pupillary dilation to permit CFP and adequate BCVA evaluation.
8. Patients who have the capacity to give informed consent and who are willing and able to comply with all study-related procedures and assessments.

Exclusion Criteria

If an individual meets any of the following criteria, he or she is ineligible for this study:
1. Concurrent disease in the study eye or structural damage, other than nAMD, that could compromise BCVA, prevent BCVA improvement, require medical or surgical intervention during the study period, confound interpretation of the results, or interfere with assessment of toxicity or CFP in the study eye. This includes, but is not limited to, the following:
   Macular edema of etiologies other than nAMD
   Clinically significant subretinal fibrosis
   Subfoveal lipid
   Cataract requiring surgery during the study period
   RPE atrophy or tear or rips involving the macula
   Clinically significant macular hole
   Clinically significant noninfectious uveitis
   Vitreomacular traction
   Clinically significant epiretinal membrane (ERM)
   Aphakia
   Pseudophakia with anterior chamber intraocular lens (A/C IOL)
2. Any ocular/intraocular/periocular infection or inflammation in either eye in the past 4 weeks prior to Screening (mild blepharitis is acceptable).
3. Subretinal hemorrhage with bleeding area disc area in the study eye.
4. History of vitrectomy in the study eye.
5. History of intraocular, periocular, or corneal surgery in the study eye within 3 months prior to Screening, or anticipated need for such surgery during the study.
6. History of panretinal photocoagulation (within 6 months) or macular laser photocoagulation (within 3 months) in the study eye prior to dosing.
7. History of corneal transplant in the study eye.
8. Concomitant use of >2 medications for the treatment of glaucoma and unstable glaucoma in the study eye (i.e., inadequate IOP control).
9. Any condition, including laboratory findings and findings in the medical history or in the pre-study assessments, that, in the opinion of the Investigator, constitutes a risk or contraindication for participation in the study or that could interfere with the study objectives, conduct, or evaluation or prevent the patient from fully participating in all aspects of the study.
10. Presence of severe myopia (−8 diopters or greater) in the study eye.

11. Current use or history of chronic therapy with systemic or topical ocular corticosteroids (defined as multiple doses taken daily for 3 or more consecutive days at any time within 6 months before enrollment). The use of intravitreal nonbiodegradable steroid implants (ex. Iluvien®, Yutiq®, Retisert®) is prohibited.
12. Significant media opacities, including cataract, which might interfere with VA, assessment of toxicity, or fundus imaging.
13. Intraocular surgery, including cataract surgery, in the study eye months of screening.
14. Known allergy to any component (phosphate buffered saline and polysorbate 80) of the compound of Formula I or clinically relevant sensitivity to fluorescein dye.
15. Female patients who are pregnant, lactating, or of childbearing potential who do not agree to use highly effective methods of birth control (e.g., progesterone-only hormonal contraception, double barrier, or intrauterine device) during the study and for 3 months following the last dose of the compound of Formula I. Postmenopausal females (>45 years old and without menses for more than 1 year) and surgically sterilized females are exempt from these requirements.
16. Male patients who do not agree to use a highly effective method of contraception during the study and for 3 months following the last dose of the compound of Formula I, if sexually active with a female partner of childbearing potential.
17. Patients who within 3 months of screening received or are concurrently on another investigational drug or vaccine study, including patients who previously received treatment in a study for the compound of Formula I.
18. Any uncontrolled medical condition, in the opinion of the Investigator, would preclude participation in this study, including, but not limited to, history of malignancy within the last 3 years (however, non-facial, basal cell carcinoma is allowed), history of myocardial infarction within the last 6 months, or concomitant therapy.

Example 4: Comparing the Ocular Pharmacokinetics and Tolerability of Two Salt Forms Following IVT Injection in New Zealand White Rabbits Evaluation of the ocular pharmacokinetics (PK) and tolerability of two salt forms (sodium salt and meglumine salt) of the Compound of Formula I following a single IVT injection in New Zealand White rabbits (non-GLP) was performed in order to understand if the meglumine salt form (Compound meglumine) behaved similarly or differently than the sodium salt form.

Two groups of 32 New Zealand white rabbits (64 animals total) received a single IVT injection of either the sodium salt form of the Compound of Formula I or the meglumine salt form (Compound meglumine) at 8 µg/eye. Animals were sacrificed at various time points post IVT injection (at 2 hours, at 24 hours, at 72 hours, at 120 hours, 168 hours, 336 hours, 504 hours, and at 672 hours). The eyes were enucleated and blood plasma was collected from auricular veins. The retina, lens and vitreous humor along with the plasma were dissected or collected and stored at −20° C. until use.

The tissue and fluid samples collected were analyzed by LC-MS/MS. Table 1 summarizes the PK findings. A similar exposure was observed in the vitreous humor and the lens as between the two salt forms. The concentration of compound in the retina was mainly below the limit of quantification (BLQ) for both salt forms tested (as indicated as "NC") thus no differences in the exposure in the retina was expected for both salt forms. The compound was BLQ in the plasma at all time points. A similar distribution of the sodium salt form and the meglumine salt form was observed in each of the ocular tissues tested. The highest exposure observed was in the vitreous humor for both salt forms. There was no systemic exposure of either salt form found. See FIG. 15.

TABLE 1

| Tissue | Formulation | Cmax (ng/mL) | Tmax (h) | T½ (h) | AUCinf (ng*h/mL) | AUC24 (ng*h/mL) |
|---|---|---|---|---|---|---|
| Vitreous Humor | Na Salt | 2210 | 2.00 | 16.33 | 36844 | 29600 |
| | Meglumine Salt | 2402 | 2.00 | 11.38 | 31940 | 27028 |
| | Ratio (Meg/Na) | 1.09 | 1.00 | 0.70 | 0.87 | 0.91 |
| Lens | Na Salt | 27.76 | 2.00 | NC | NC | 226.67 |
| | Meglumine Salt | 12.79 | 2.00 | NC | NC | 241.35 |
| | Ratio (Meg/Na) | 0.46 | 1.00 | NC | NC | 1.06 |
| Retina | Na salt | 0.97 | 2.00 | NC | NC | NC |
| | Meglumine Salt | 5.07 | 2.00 | NC | NC | NC |
| | Ratio (Meg/Na) | 5.21 | 1.00 | NC | NC | NC |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a patient suffering from a retinal vasculopathy comprising administering to the patient a therapeutically effective dose of a meglumine salt of a compound of Formula I (Compound-meglumine):

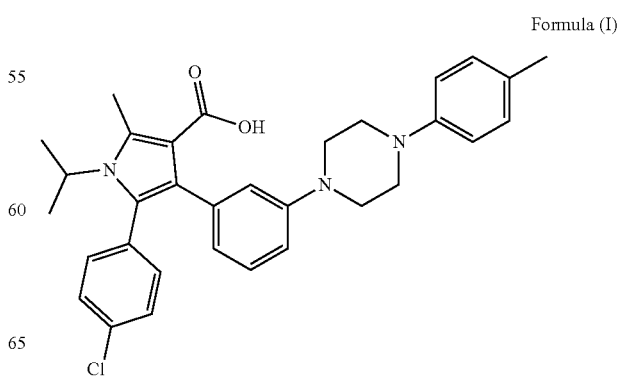

Formula (I)

-continued

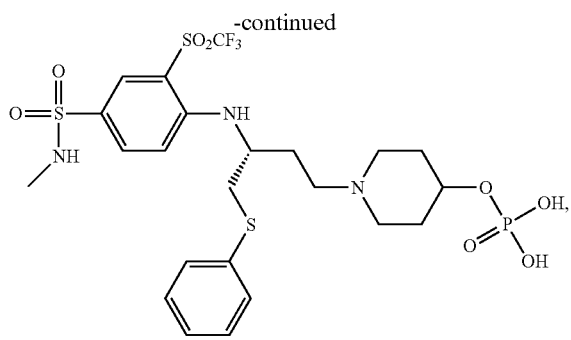

(R)-5-(4-chlorophenyl)-1-isopropyl-2-methyl-4-(3-(4-(4-((4-((1-(phenylthio)-4-(4-((phosphonooxy)methyl)piperidin-1-yl)butan-2-yl)amino)-3-((trifluoromethyl)sulfonyl)phenyl)sulfonamido)phenyl)piperazin-1-yl)phenyl)-1H-pyrrole-3-carboxylic acid,
wherein the therapeutically effective dose is up to 10 ug of the Compound-meglumine is administered intravitreally (IVT) per eye.

2. The method of claim 1, wherein the patient has a baseline best corrected visual acuity (BCVA) between 70 to 20 Early Treatment Diabetic Retinopathy Study (ETDRS) letters or a baseline 20/40 to 20/400 on the Snellen chart.

3. The method of claim 1, wherein the patient had been previously treated with an anti-vascular endothelial growth factor (anti-VEGF) treatment at baseline.

4. The method of claim 3, wherein the previous treatment with an anti-VEGF treatment occurred in the preceding 6-month period.

5. The method of claim 4, the wherein the patient also presented with a central subfield thickness (CST) of ≥300 μm as measured by SD-OCT at baseline, or of ≥350 μm as measured by SD-OCT at baseline.

6. The method of claim 1, wherein the patient has a hemoglobin A1C (HbA 1C) of <12% at baseline, of <11% at baseline, of <10% at baseline, of <9% at baseline, of <8% at baseline, or of <7% at baseline.

7. The method of claim 1, wherein the patient has an intraocular pressure (TOP) of ≤23 mmHg at baseline, of ≤22 mmHg at baseline, of ≤21 mmHg at baseline, of ≤20 mmHg at baseline, of ≤19 mmHg at baseline, of ≤18 mmHg at baseline, of ≤17 mmHg at baseline, of ≤16 mmHg at baseline, of ≤15 mmHg at baseline, of ≤14 mmHg at baseline, of ≤13 mmHg at baseline, of ≤12 mmHg at baseline, of ≤11 mmHg at baseline, of ≤10 mmHg at baseline, of ≤9 mmHg at baseline, of ≤8 mmHg at baseline, of ≤7 mmHg at baseline, of ≤6 mmHg at baseline, of ≤5 mmHg at baseline, of ≤4 mmHg at baseline, of ≤3 mmHg at baseline, of ≤2 mmHg at baseline, of ≤1 mmHg at baseline.

8. The method of claim 1, wherein the therapeutically effective dose of the Compound-meglumine is 2.5 ug, 3 ug, 4 ug, 5 ug, 6 ug, 7 ug, 8 ug, 9 ug, or 10 ug per eye.

9. The method of claim 1, wherein the therapeutically effective dose of the Compound-meglumine is between 2.5 μg 3 μg per eye, between 3-4 μg per eye, between 4-5 μg per eye, between 5 μg-6 μg per eye, between 6-7 μg per eye, between 7 μg-8 μg per eye, between 8μg-9 μg per eye, or between 9 μg-10 μg per eye.

10. The method of claim 1, wherein the therapeutically effective dose of the Compound-meglumine is between 2-4 ug per eye, is between 3-5 ug per eye, is between 4-6 ug per eye, is between 5-7 ug per eye, is between 6- 8ug per eye, is between 7- 9ug per eye, or is between 8- 10ug per eye.

11. The method of claim 1, wherein the Compound-meglumine is administered into the patient's eye first as a loading dose, prior to administering the therapeutically effective dose.

12. The method of claim 11, wherein the loading dose of the Compound-meglumine is between 2.5 μg-3 μg per eye, between 3 μg-4 μg per eye, between 4 μg-5 μg per eye, between 5 μg-6 μg per eye, between 6 μg-7 μg per eye, between 7 μg-8 μg per eye, between 8 μg-9 μg per eye, or between 9 μg-10 μg.

13. The method of claim 11, wherein the loading dose of the Compound-meglumine is between 2-4 ug per eye, is between 3-5 ug per eye, is between 4-6 ug per eye, is between 5-7 ug per eye, is between 6-8 ug per eye, is between 7-9 ug per eye, or is between 8-10 ug per eye.

14. The method of claim 8, wherein the therapeutically effective dose of the Compound-meglumine is administered intravitreally into the patient's eye every 2 months, every 3 months, every 4 months, every 5 months, every 6 months, every 7 months, every 8 months, every 9 months, every 10 months, every 11 months, every 12 months.

15. The method of claim 8, wherein the therapeutically effective dose of the Compound-meglumine is administered intravitreally into the patient's eye between every 2-3 months, between every 3-4 months, between every 5-6 months, between every 6-7 months, between every 8-9 months, between every 9-10 months, between every 11-12 months.

16. The method of claim 1, wherein the therapeutically effective dose of the Compound-meglumine is administered intravitreally into the patient's eye as a single dose every 2 months, a single dose every 3 months, a single dose every 4 months, a single dose every 5 months, a single dose every 6 months, a single dose every 7 months, a single dose every 8 months, a single dose every 9 months, a single dose every 10 months, a single dose every 11 months, or a single dose every 12 months.

17. The method of claim 1, wherein the therapeutically effective dose of the Compound-meglumine is administered intravitreally into the patient's eye as a single dose between every 2- 3 months, as a single dose between every 3-4 months, as a single dose between every 5-6 months, as a single dose between every 6-7 months, as a single dose between every 8-9 months, as a single dose between every 9-10 months, as a single dose between every 11-12 months.

18. The method of claim 8, wherein the therapeutically effective dose of the Compound-meglumine is administered intravitreally into the patient's eye once as a single dose is not in conjunction with a prior loading dose.

19. The method of claim 11, wherein the loading dose, administered intravitreally into the patient's eye, is administered as one monthly IVT injection for 2 months, or one monthly IVT injection for 3 months, or at least one IVT injection over 2 months, or at least two IVT injections over 2 months, or at least three IVT injections over 2 months, or at least three IVT injections over 3 months, or at least two IVT injections over 3 months.

20. The method of claim 8, wherein the patient demonstrates a CST reduction of at least 40 μm from baseline, at least 50 μm from baseline, at least 60 μm from baseline, at least 70 μm from baseline, at least 80 μm from baseline, at least 90 μm from baseline, as measured by SD-OCT.

21. The method of claim 8, wherein the patient further demonstrates an absence of macular fluid as assessed by SD-OCT as compared to baseline.

22. The method of claim 8, wherein the patient further demonstrates an absence of exudation as assessed by SD-OCT as compared to baseline.

23. The method of claim 14, wherein the patient does not require more than 2 anti-VEGF treatment rescue, or does not require more than 3 anti-VEGF treatment rescue, or does not require more than 4 anti-VEGF treatment rescue, or does not require more than 5 anti-VEGF treatment rescue.

24. The method of claim 23, wherein the patient does not require any anti-VEGF treatment rescue.

25. The method of claim 14, wherein the patient demonstrates an improvement in at least 5 ETDRS letter improvement on BCVA over baseline, or at least 6 ETDRS letter improvement on BCVA over baseline, or at least 7 ETDRS letter improvement on BCVA over baseline, or at least 8 ETDRS letter improvement on BCVA over baseline, or at least 9 ETDRS letter improvement on BCVA over baseline, or at least 10 ETDRS letter improvement on BCVA over baseline, at least 15 ETDRS letter improvement on BCVA over baseline, or at least 20 ETDRS letter improvement on BCVA over baseline.

26. The method of claim 14, wherein the patient demonstrates an improvement of between 5-7 ETDRS letter improvement on BCVA over baseline, of between 6-8 ETDRS letter improvement on BCVA over baseline, of between 7-9 ETDRS letter improvement on BCVA over baseline, of between 10-15 ETDRS letter improvement on BCVA over baseline, of between 15-20 ETDRS letter improvement on BCVA over baseline, of between 20-25 ETDRS letter improvement on BCVA over baseline, of between 25-30 ETDRS letter improvement on BCVA over baseline.

27. The method of claim 14, wherein the patient demonstrates at least a 0.10 mm2 reduction of ocular avascular area over baseline, or at least a 0.20 $mm^2$ reduction of ocular avascular area over baseline, or at least a 0.30 $mm^2$ reduction of ocular avascular area over baseline, or at least a 0.40 $mm^2$ reduction of ocular avascular area over baseline, or at least a 0.50 $mm^2$ reduction of ocular avascular area over baseline, or at least a 0.60 $mm^2$ reduction of ocular avascular area over baseline, or at least a 0.70 $mm^2$ reduction of ocular avascular area over baseline, or at least a 0.80 $mm^2$ reduction of ocular avascular area over baseline, or at least a 0.90 $mm^2$ reduction of ocular avascular area over baseline, or at least a 1.0 $mm^2$ reduction of ocular avascular area over baseline, all as measured by fluorescence angiography (FA) or optical coherence tomography angiography (OCT-A).

28. The method of claim 14, wherein the patient has a 2-step improvement in diabetic retinopathy severity scale (DRSS) over baseline.

29. The method of claim 14, wherein the patient demonstrates a regression in neovascularization over baseline, as measured by FA or OCT-A.

30. The method of claim 1, wherein the retinal vasculopathy is diabetic macular edema (DME).

31. The method of claim 1, wherein the retinal vasculopathy is diabetic retinopathy (DR).

32. The method of claim 31, wherein the patient also presented with nonproliferative diabetic retinopathy at baseline.

33. The method of claim 31, wherein the patient also presented with proliferative diabetic retinopathy at baseline.

* * * * *